(12) United States Patent
Getautis et al.

(10) Patent No.: US 11,329,229 B2
(45) Date of Patent: May 10, 2022

(54) HOLE TRANSPORTING ORGANIC MOLECULES CONTAINING ENAMINE GROUPS FOR OPTOELECTRONIC AND PHOTOELECTROCHEMICAL DEVICES

(71) Applicants: KAUNO TECHNOLOGIJOS UNIVERSITETAS, Kaunas (LT); ECOLE POLYTECHNIQUE FEDERALE DE LAUSANNE (EPFL), Lausanne (CH)

(72) Inventors: Vytautas Getautis, Kaunas (LT); Maryte Daskeviciene, Jonava (LT); Tadas Malinauskas, Kaunas (LT); Mohammad Khaja Nazeeruddin, Ecublens (CH); Sanghyun Paek, Seoul (KR); Kasparas Rakstys, Vilnius (LT)

(73) Assignees: KAUNO TECHNOLOGIES UNIVERSITETAS, Kaunas (LT); ECOLE POLYTECHNIQUE FEDERALE DE LAUSAANE (EPFL), Lausaane (CH)

( * ) Notice: Subject to any disclaimer, the term of this patent is extended or adjusted under 35 U.S.C. 154(b) by 147 days.

(21) Appl. No.: 16/334,352
(22) PCT Filed: Sep. 15, 2017
(86) PCT No.: PCT/IB2017/055587
§ 371 (c)(1),
(2) Date: Mar. 18, 2019
(87) PCT Pub. No.: WO2018/051278
PCT Pub. Date: Mar. 22, 2018

(65) Prior Publication Data
US 2019/0229272 A1 Jul. 25, 2019

(30) Foreign Application Priority Data
Sep. 19, 2016 (LT) ..................... 2016 515

(51) Int. Cl.
*H01L 51/00* (2006.01)
*C07C 217/60* (2006.01)
(Continued)

(52) U.S. Cl.
CPC ........ *H01L 51/0061* (2013.01); *C07C 217/60* (2013.01); *C07C 217/84* (2013.01);
(Continued)

(58) Field of Classification Search
None
See application file for complete search history.

(56) References Cited

U.S. PATENT DOCUMENTS

| 4,808,505 A | 2/1989 | Ueda |
| 5,098,810 A | 3/1992 | Mizuguchi et al. |

(Continued)

FOREIGN PATENT DOCUMENTS

| EP | 0613466 A1 | 9/1994 |
| EP | 0758337 A1 | 2/1997 |

(Continued)

OTHER PUBLICATIONS

English language Abstract of JP H10152678 A (Jun. 9, 1998).
(Continued)

*Primary Examiner* — Clinton A Brooks
(74) *Attorney, Agent, or Firm* — Hershkovitz & Associates, PLLC; Abe Hershkovitz

(57) ABSTRACT

The present invention relates to a compound of formula (I) based on enamine derivatives and used as organic hole conductors or hole transporting material in an optoelectronic or photoelectrochemical device. The present invention relates to the hole transporting compounds based on enamine derivatives for efficiency perovskite or dye sensitized solar cells and optoelectronic devices, organic light-emitting diode (OLED), field-effect transistors (FET).

21 Claims, 1 Drawing Sheet

(51) Int. Cl.

| | |
|---|---|
| *C07D 209/88* | (2006.01) |
| *H01L 51/42* | (2006.01) |
| *C07C 217/84* | (2006.01) |
| *H01G 9/20* | (2006.01) |
| *H01L 51/50* | (2006.01) |

(52) U.S. Cl.
CPC ......... *C07D 209/88* (2013.01); *H01G 9/2009* (2013.01); *H01L 51/0059* (2013.01); *H01L 51/4226* (2013.01); *H01L 51/005* (2013.01); *H01L 51/0072* (2013.01); *H01L 51/5056* (2013.01); *Y02E 10/549* (2013.01)

(56) References Cited

U.S. PATENT DOCUMENTS

| | | |
|---|---|---|
| 2004/0085619 A1 | 5/2004 | Wu et al. |
| 2018/0033973 A1 | 2/2018 | Gratia et al. |

FOREIGN PATENT DOCUMENTS

| | | |
|---|---|---|
| EP | 0983282 A1 | 3/2000 |
| EP | 1622178 A1 | 2/2006 |
| EP | 1990373 A1 | 11/2008 |
| EP | 2511924 A1 | 10/2012 |
| EP | 2703468 A1 | 3/2014 |
| EP | 2883915 A1 | 6/2015 |
| EP | 2937399 A1 | 10/2015 |
| JP | H10152678 A | 6/1998 |
| JP | H1143458 A | 2/1999 |
| JP | H11335336 A | 12/1999 |
| JP | 2000007625 A | 1/2000 |
| JP | 2000159732 A | 6/2000 |
| JP | 2002229231 A | 8/2002 |
| WO | WO 94/04497 A1 | 3/1994 |
| WO | WO 95/29924 A1 | 11/1995 |
| WO | WO 98/50393 A1 | 11/1998 |
| WO | WO 2006/038823 A1 | 4/2006 |
| WO | WO 2007/100033 A1 | 9/2007 |
| WO | WO 2009/098643 A2 | 8/2009 |
| WO | WO 2009/107100 A2 | 9/2009 |
| WO | WO 2010/055471 A1 | 5/2010 |
| WO | WO 2011/039715 A1 | 4/2011 |
| WO | WO 2013/057538 A1 | 4/2013 |
| WO | WO 2014/033582 A1 | 3/2014 |
| WO | WO 2015/087210 A1 | 6/2015 |
| WO | WO 2015/161989 A1 | 10/2015 |
| WO | WO 2016/139570 A1 | 9/2016 |

OTHER PUBLICATIONS

English language Abstract of JP H11335336 A (Dec. 7, 1999).
English language Abstract of JP H1143458 A (Feb. 16, 1999).
English language Abstract of JP 2000007625 A (Jan. 11, 2000).
English language Abstract of JP 2000159732 A (Jun. 13, 2000).
English language Abstract of JP 2002229231 A (Aug. 14, 2002).
Machine-generated English language translation of description and claims of WO 2007/100033 A1 (Sep. 7, 2007).
M. Daskeviciene, et al., "Carbazole-based enamine: Low-cost and efficient hole transporting material for perovskite solar cells", Nano Energy, (Jan. 9, 2017), vol. 32, doi:10.1016/j.nanoen.2017.01.015, ISSN 2211-2855, pp. 551-557.
G. Tamulaitis, G. Juska, "Energy saving semiconducting technologies", Vilnius: Progretus, 2008, pp. 116-121, ISBN 9789955781134.
B. Saparovand D. B. Mitzi, Chemical Reviews, "Organic-Inorganic Perovskites: Structural Versatility for Functional Materials Design", 2016, 116, p. 4558-4596.
C. Zuo, H. J. Bolink, H. Han, J. Huang, D. Cahen, and L. Ding, "Advances in Perovskite Solar Cells", Advanced Science, 2016, 3, 1500324.
M. Saliba, S. Orlandi, T. Matsui, S. Aghazada, M. Cavazzini, J. P. Correa-Baena, P. Gao, R. Scopelliti, E. Mosconi, K. H. Dahmen, F. De Angelis, A. Abate, A. Hagfeldt, G. Pozzi, M. Graetzel, M. K. Nazeeruddin, "A molecularly engineered hole-transporting material for efficient perovskite solar cells", Nature Energy, 2016, vol. 1, 15017.
Y. Shi, K. Hou, Y. Wang, K. Wang, H. C. Ren, M. Y. Pang, F. Chen, S. Zhang, "Two methoxyaniline-substituted dibenzofuran derivatives as hole-transport materials for perovskite solar cells", Journal of Materials Chemistry A, 2016, 4, pp. 5415-5422.
T. P. I. Saragi, T. Spehr, A. Siebert, T. Fuhrmann-Lieker, J. Salbeck, "Spiro Compounds for Organic Optoelectronics", Chemical Reviews, 2007, 107, pp. 1011-1065.
D. Bi, B. Xub, p. Gao, L. Sun, M. Grätzel, A. Hagfeldt, "Facile synthesized organic hole transporting material for perovskite solar cell with efficiency of 19.8%", Nano Energy, 2016, 23, pp. 138-144.
W. S. Yang, J. H. Noh, N. J. Jeon, Y. C. Kim, S. Ryu, J. Seo, S. I. Seok, "High-performance photovoltaic perovskite layers fabricated through intramolecular exchange", Science, 2015, vol. 348, 1234-1237.
E. Puodziukynaite et al., "Carbazole-based bis(enamines) as effective charge-transporting amorphous molecular materials", Synthetic Metals, vol. 158, 2008, pp. 993-998.
E. Miyamoto, Y. Yamaguchi, M. Masaaki, "Ionization Potential of Organic Pigment Film by Atmospheric Photoelectron Emission Analysis", Electrophotography, 1989, vol. 28, pp. 364-370.
Vaezi-Nejad, S. M., "Xerographic time of flight experiment for the determination of drift mobility in high resistivity semiconductors", International Journal of Electronics, 1987, 62, No. 3, pp. 361-384.
T. J. Jacobsson, J.P. Correa-Baena, M. Pazoki, M. Saliba, K. Schenk, M. Grätzel and A. Hagfeldt, Exploration of the compositional space for mixed lead halogen perovskites for high efficiency solar cells, Energy & Environmental Science, 2016, 9, pp. 1706-1724.
International Search Report in International Application No. PCT/IB2017/055587, dated Mar. 26, 2018.
International Preliminary Report on Patentability in International Application No. PCT/IB2017/055587, dated Mar. 19, 2019.

US 11,329,229 B2

HOLE TRANSPORTING ORGANIC MOLECULES CONTAINING ENAMINE GROUPS FOR OPTOELECTRONIC AND PHOTOELECTROCHEMICAL DEVICES

TECHNICAL FIELD

The present invention relates to hole transporting compound containing enamine moieties, to organic hole conductors and to hole transporting material comprising such a compound, to optoelectronic photoelectrochemical devices comprising such hole transporting material or hole transporting compound, in particular photovoltaic devices, organic-inorganic perovskite films or layer photovoltaic devices, p-n heterojunctions, dye-sensitized solar cells, organic solar cells and solid state solar cells. The invention is also concerned with a method of preparing such organic hole conductors, layers, and optoelectronic devices.

Prior Art and the Problem Underlying the Invention

In the recent decades, a strong interest in renewable energy sources and the most potent among them—Sun. Every hour our planet receives the amount of energy equal to the yearly consumption by our civilization (G. Tamulaitis, G. Juska. Energy saving semiconducting technologies. Vilnius: Progretus, 2008, p.p. 116-121. ISBN 9789955781134). Therefore, technological advances in the field of photovoltaics (PV) could potentially solve current energy demands. The conversion of solar energy to electrical current using thin film third generation photovoltaics is being widely explored for the last two decades. The sandwich/monolithic-type PV devices, consisting of a mesoporous photoanode with an organic/inorganic light harvester, redox electrolyte/solid-state hole conductor, and counter electrode, have gained significant interest due to the ease of their fabrication, the flexibility in the selection of materials and the low cost effective production.

Although organic-neorganic perovskites are known from the XIX century, currently they have attracted substantial attention in the field of photovoltaics and optoelectronics (B. Saparov and D. B. Mitzi. *Chem. Rev.* 2016, 116, 4558-4596). During recent five years efficiencies of the PV devices containing hybrid organic-inorganic perovskites have skyrocketed and reached values over 20% (C. Zuo, H. J. Bolink, H. Han, J. Huang, D. Cahen, and L. Ding. *Adv. Sci.* 2016, 3, 1500324. M. Saliba, S. Orlandi, T. Matsui, S. Aghazada, M. Cavazzini, J. P. Correa-Baena, P. Gao, R. Scopelliti, E. Mosconi, K. H. Dahmen, F. De Angelis, A. Abate, A. Hagfeldt, G. Pozzi, M. Graetzel, M. K. Nazeeruddin, *Nat. Energy* 2016, 1, 15017) and the record perovskite-containing PV device performance currently is 22.1 (www.nrel.gov/ncpv/images/efficiency_chart.jpg, accessed on Sep. 5, 2017).

Hole transporting materials is one of the quintessential components required for the efficient PV devices. These materials are responsible for the transport of the photogenerated carriers from the absorber towards the electrode. Hole transporting materials should demonstrate sufficient charge transport properties, adequate energy levels, especially HOMO level and good thermal stability (Y. Shi, K. Hou, Y. Wang, K. Wang, H. C. Ren, M. Y. Pang, F. Chen, S. Zhang *J Mater. Chem. A*, 2016, 4, 5415-5422). And these materials are a weak spot in whole PV device. Despite significant research efforts devoted towards development of new hole transporting materials, the field is still dominated by spiro-OMeTAD (2,2',7,7'-tetrakis(N,N-di-p-methoxyphenylamine)-9,9'-spirobifluorene) as organic hole transporting material (HTM). Currently the best efficiencies in dye sensitized solar cells with solid hole conductors are obtained with the compound spiro-MeOTAD. Unfortunately synthesis procedure of this HTM is a lengthy and complicated procedure requiring the use of expensive Pd catalysts, sensitive (n-butyllithium, Grignard reagents), aggressive ($Br_2$) reagents and low temperatures (−78° C.) (T. P. I. Saragi, T. Spehr, A. Siebert, T. Fuhrmann-Lieker, J. Salbeck, *Chem. Rev.*, 2007, 107, 1011-1065). Furthermore, in order to ensure maximum performance, spiro-MeOTAD must be purified via sublimation, inevitably driving up the cost of the material. Synthetic work undertaken to replace spiro-MeOTAD has yielded several groups of HTM molecules demonstrating good charge mobility and comparable performance in the PV devices (WO2015161989, EP2937399, D. Bi, B. Xub, P. Gao, L. Sun, M. Grätzel, A. Hagfeldt, *Nano Energy*, 2016, 23, 138-144), however vast majority of these derivatives still require expensive catalysts and multistep synthesis procedures.

One of the possible alternatives could be high-mobility organic polymers such as polypyrrole, poly(3,4-ethylenedioxythiophene), carbazole-based polymers, polyaniline, poly(4-undecyl-2,2'-bithiophene), poly(-octylthiophene), poly(triphenyldiamine) and poly(N-vinylcarbazole). Unfortunately, performance of the majority of the investigated polymers falls short of that of spiro-MeOTAD. The only well-performing material know so far is poly[bis(4-phenyl)(2,4,6-trimethylphenyl)amine] (W. S. Yang, J. H. Noh, N. J. Jeon, Y. C. Kim, S Ryu, J. Seo, S. I. Seok, *Science,* 2015, 348, 1234.), practical application of which is hampered by high cost and reproducability issues.

The synthesis process of hole transporting material involves expensive starting material compounds being not commercially available, very low temperature of reaction step, complexity, aggressive reagents and numerous steps (e.g. 5 steps for the Spiro-OMetTAD synthesis). Thus, the synthesis process is lengthy, time-consuming and expensive and causes non-negligible environmental impact. The invention pursues to provide an efficient solar cell, which can be rapidly prepared in an efficient way, using readily available or low cost materials, using a short manufacturing procedure based on industrially known manufacturing step, keeping the material costs and the material impact on the environment very low.

SUMMARY OF THE INVENTION

The purpose of present invention is to provide new hole transporting organic compounds with suitable energetic levels and, which does not require a step of sublimation during its purification after its synthesis as it is the case of the synthesis of spiro-OMeTAD and presents ease to be synthesized.

The present invention also pursues to provide new hole transporting material, which provides higher power conversion efficiency (PCE) to photovoltaic devices comprising perovskite or organic or organometallic dyes as sensitizer or light absorbing material as well as to further optoelectronic devices Organic Light Emitting Diodes (OLED), Field Effect Transistors (FET). Said purpose is achieved by entire of features indicated in the claims.

The main object of the proposed invention is new compounds with enamine groups of the invention of formula (I):

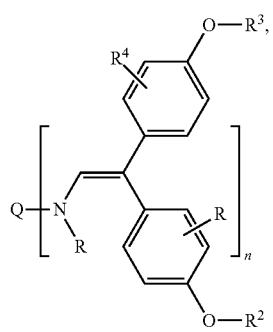

(I)

wherein
n is 1, 2, 3, 4, 5, 6, 7 or 8;
Q is a mono- or polycyclic system comprising at least one pair of a conjugated double bond (—C=C—C=C—), the polycyclic system comprising fused aromatic rings or monocyclic aromatic rings bound together by covalent bond or heteroaromatic system with N, O, S, Se, Si heteroatoms. Said mono- or polycyclic system being substituted by H, halogen, cyano group, C1-C20 cyanoalkyl group, C1-C20 alkyl, C1-C20 alkoxy group, C1-C20 alkoxyalkyl, C1-C20 haloalkyl group, C1-C20 haloalkoxyalkyl, wherein said cyanoalkyl, alkyl, alkoxy, alkoxyalkyl, haloalkyl, haloalkoxyalkyl, C4-C20 aryl, C4-C20 alkylaryl, C4-C20 alkoxyaryl C4-C20 alkenylarylalkyl, C4-C20 alkoxyarylalkenyl, C4-C20 bisalkoxyarylalkenyl groups.

If they comprise 3 or more carbons, may be linear, branched or cyclic, wherein halogen is selected from Cl, F, Br, or I;

R is a substituent, on each occurrence, identically or differently selected from C1-C20 alkyl, C2-C20 alkenyl, C4-C20 arylalkenyl, C4-C20 aryl groups. Said aryl and arylalkenyl groups could be unsubstituted on substituted with C1-C20 alkyl or C1-C20 alkoxy groups, if they comprise 3 or more carbons, may be linear, branched or cyclic;

$R^1$, $R^2$, $R^3$, $R^4$ are independent one from another and selected from hydrogen, halogen, cyano, C1-C20 cyanoalkyl, C1-C20 alkyl, C1-C20 alkoxy, C1-C20 alkoxyalkyl, C1-C20 haloalkyl, C1-C20 haloalkoxyalkyl groups. If they comprise 3 or more carbons, may be linear, branched or cyclic, wherein halogen is selected from Cl, F, Br, or I.

According to a further embodiment, the hole transporting compounds with enamine groups of the invention of formula (I) is selected from, but not limited to, a compound according to any one of formulae (1) to (54):

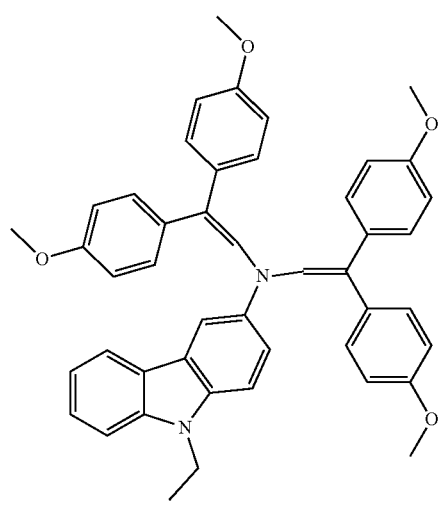

(1)

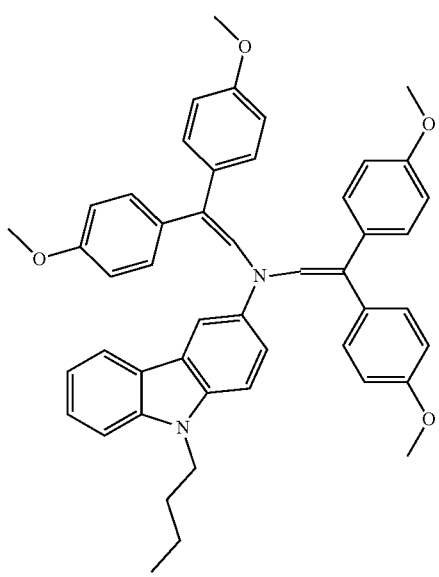

(2)

-continued
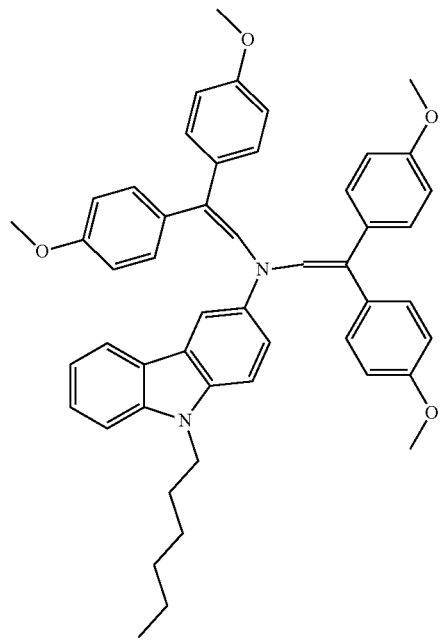
(3)
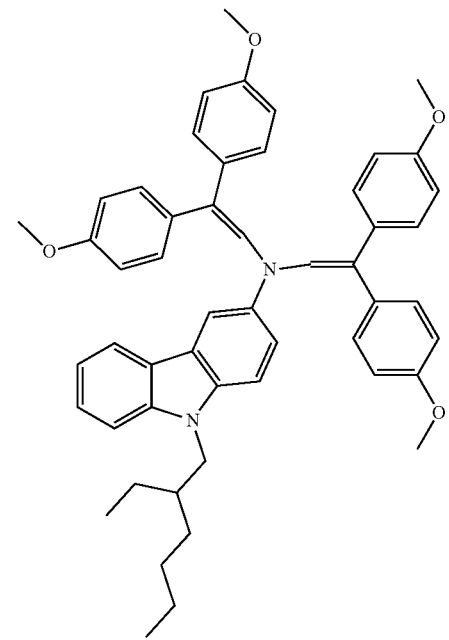
(4)
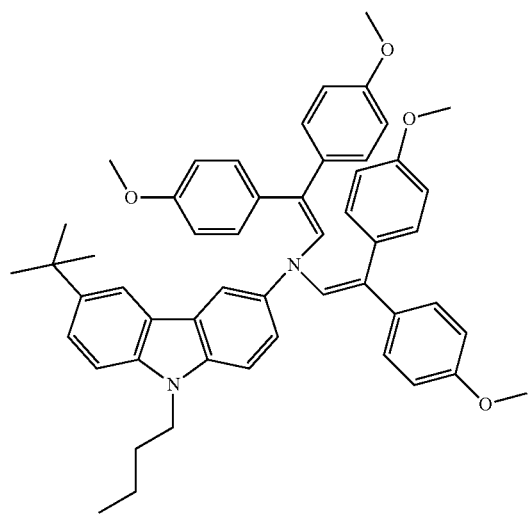
(5)
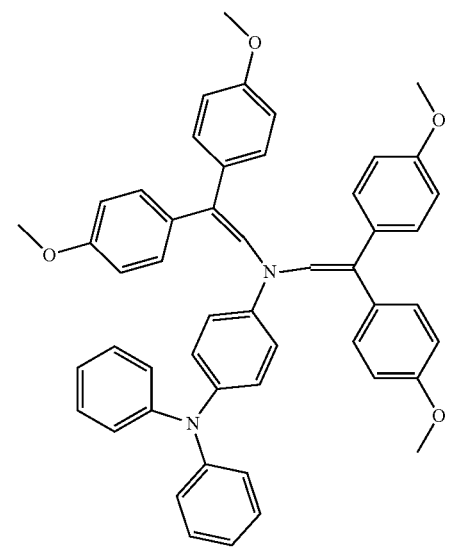
(6)
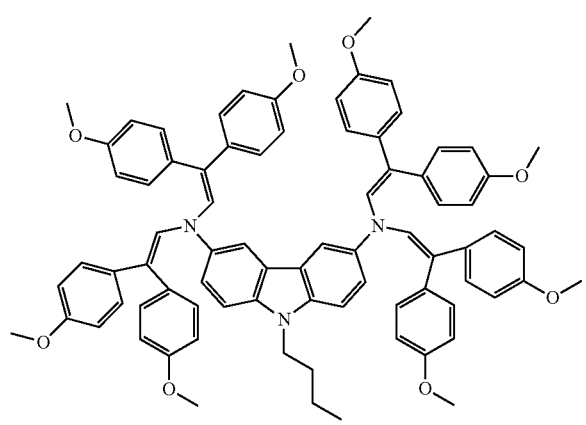
(7)
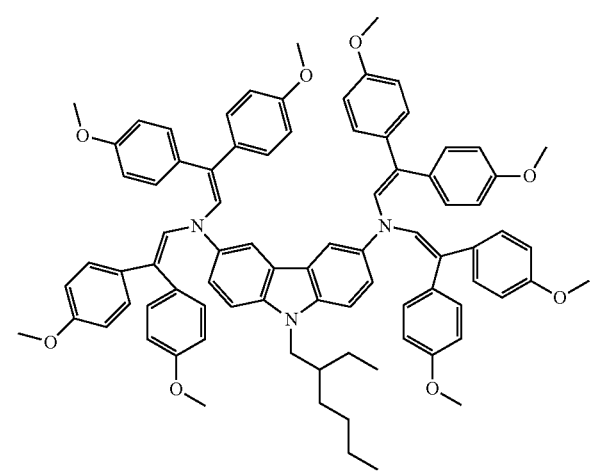
(8)

-continued
(9)
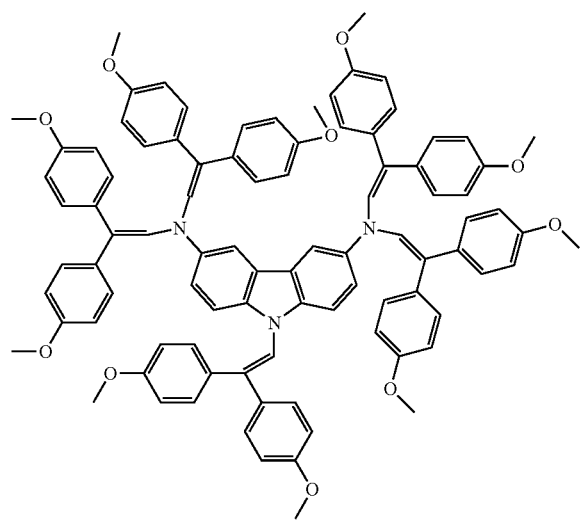
(10)
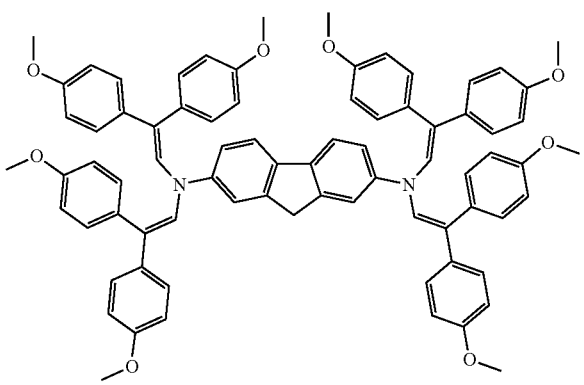
(11)
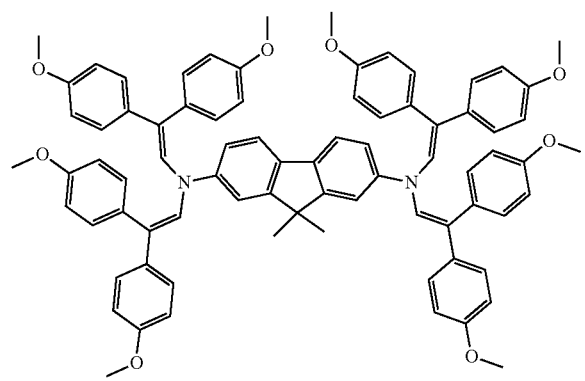
(12)
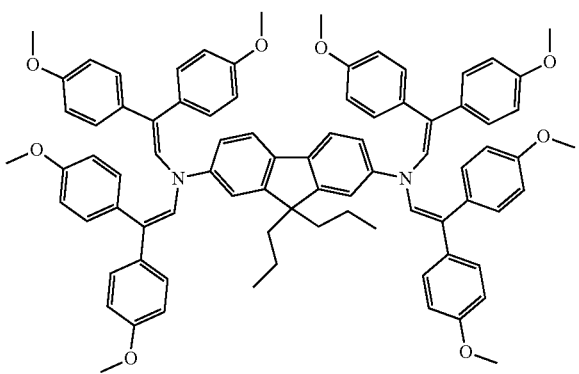
(13)
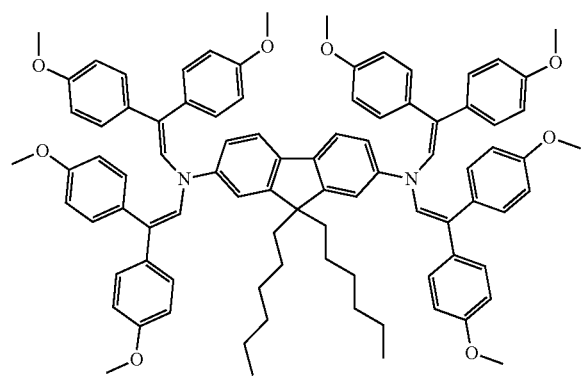
(14)
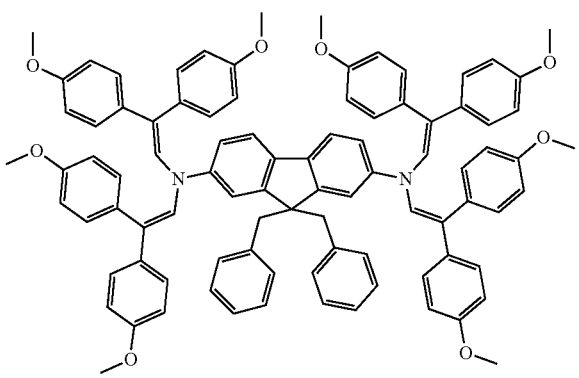

-continued
(15)
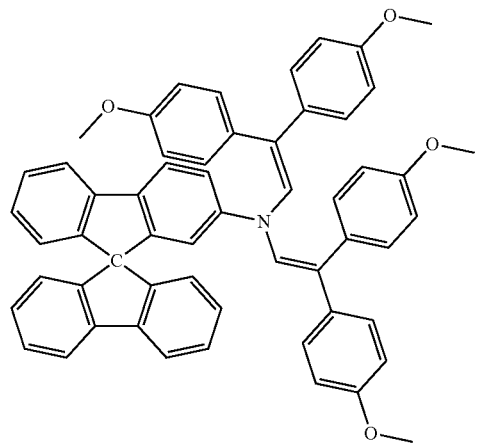
(16)
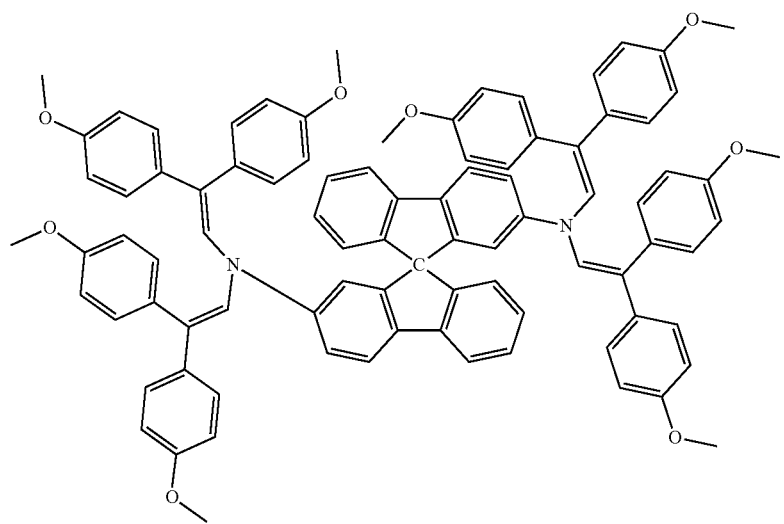
(17)
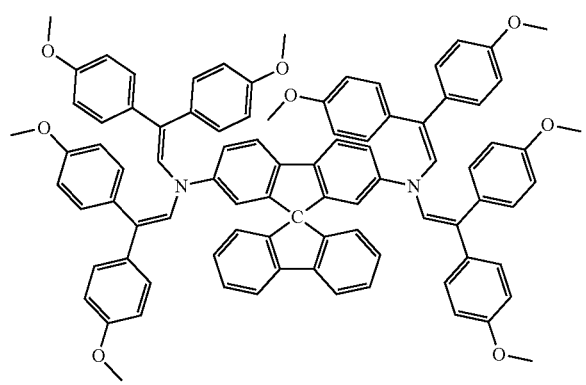
(18)
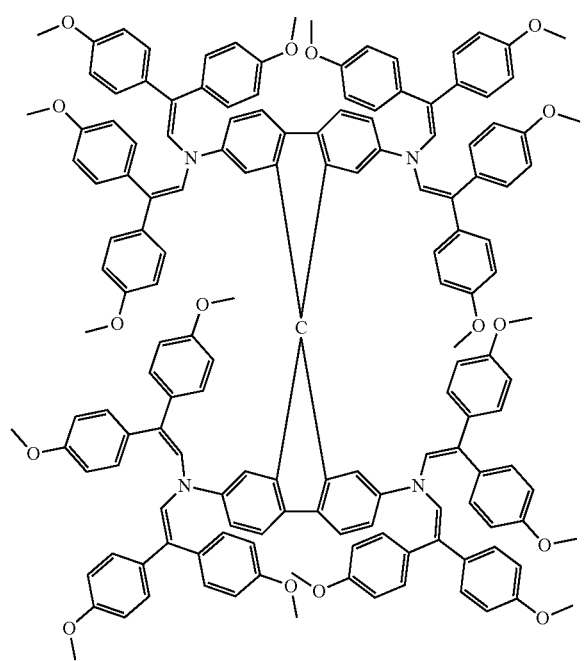

(19)
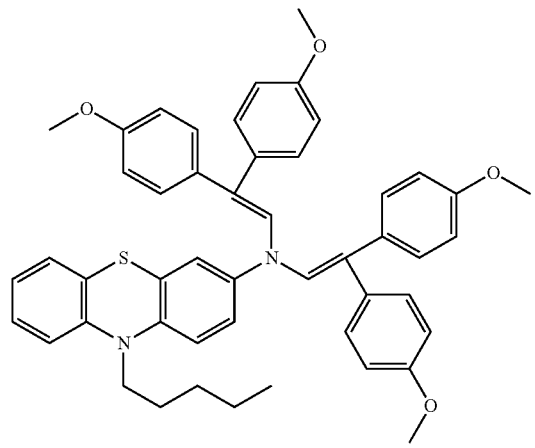
(20)
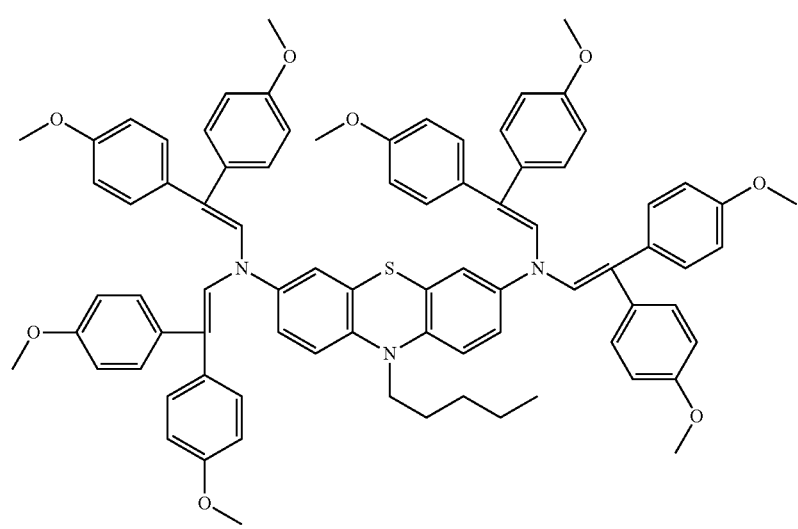
(21)
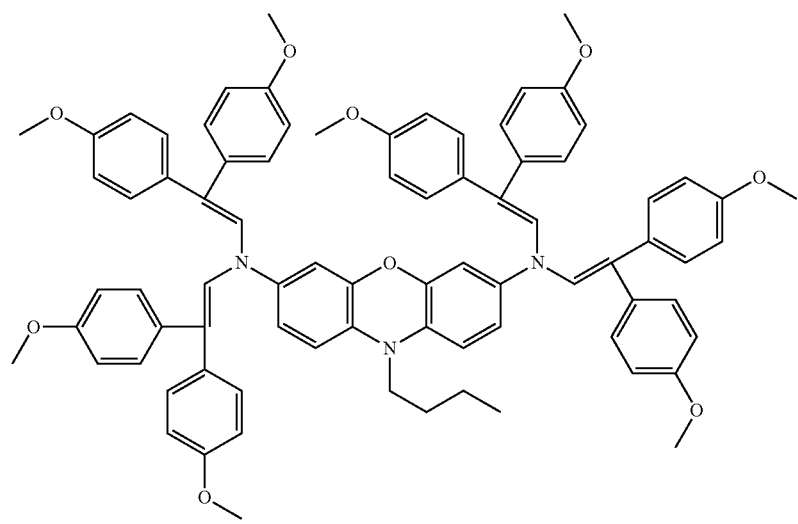

-continued
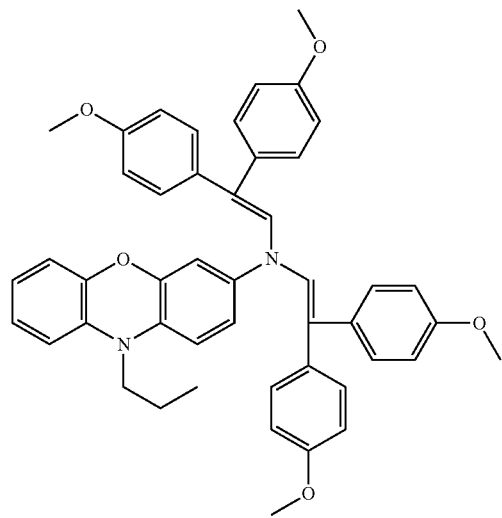
(22)
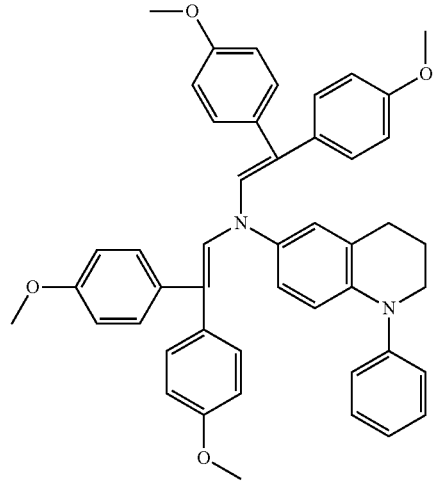
(23)
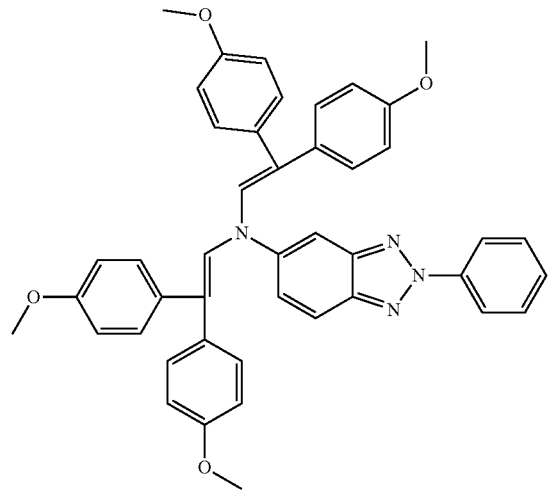
(24)
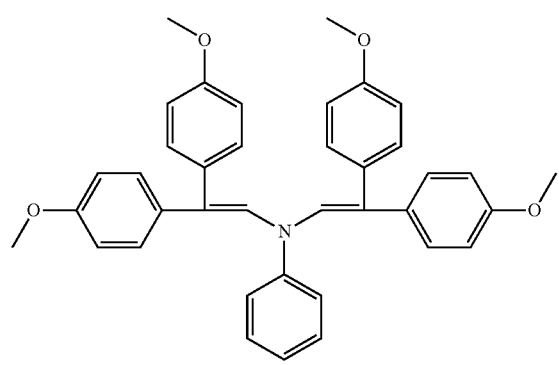
(26)
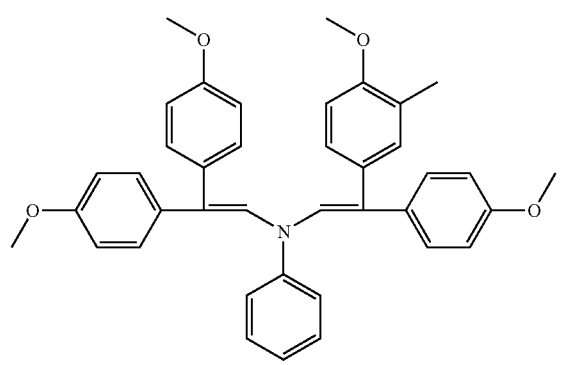
(27)

-continued
(28)
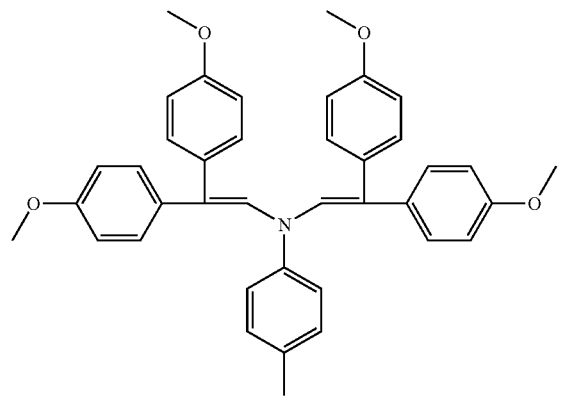
(29)
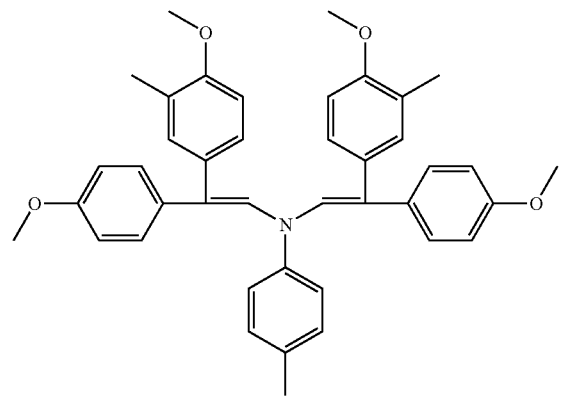
(30)
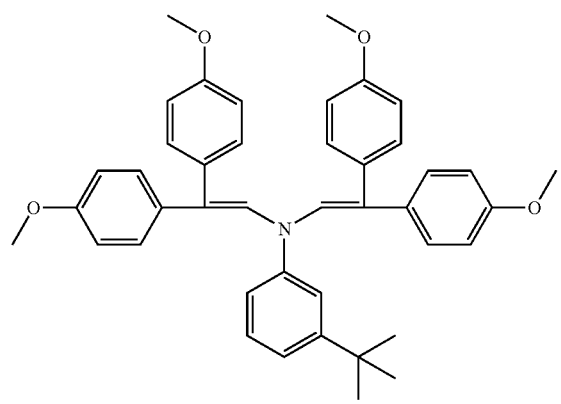
(31)
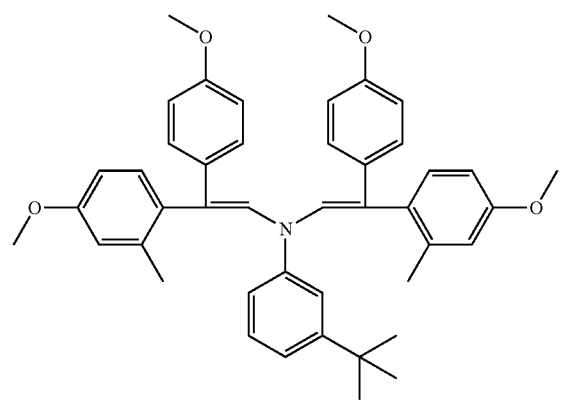
(32)
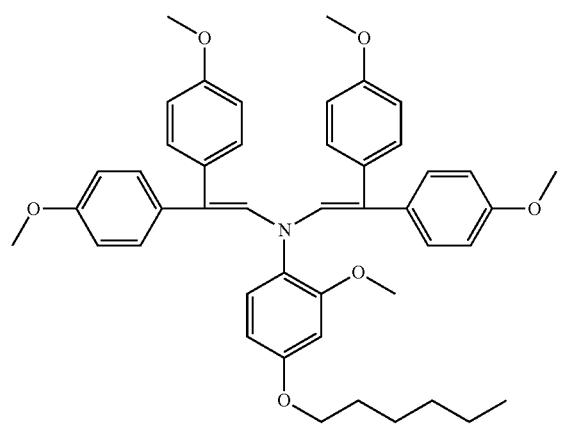
(33)
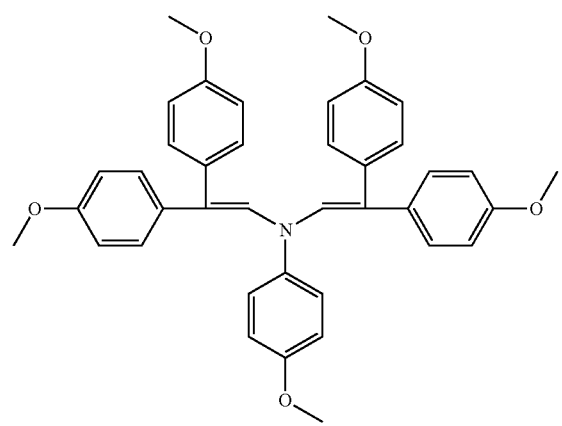

-continued
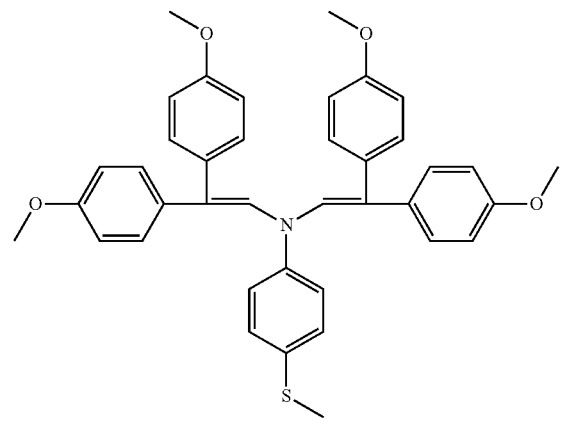
(34)
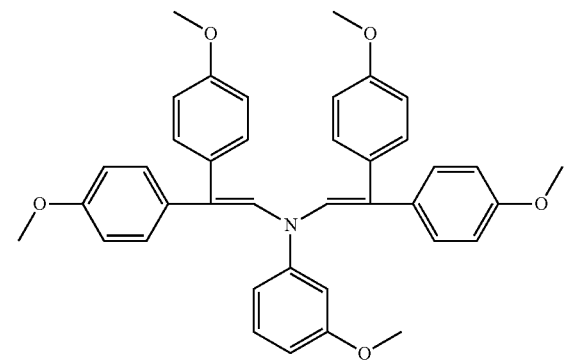
(35)
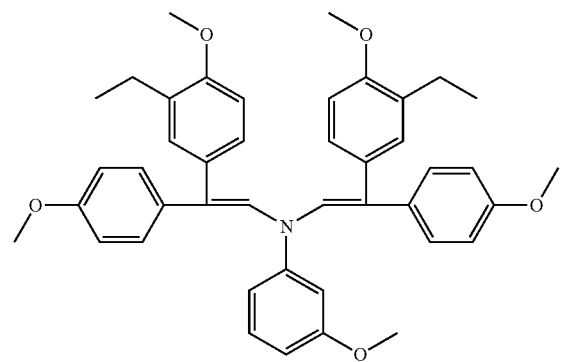
(36)
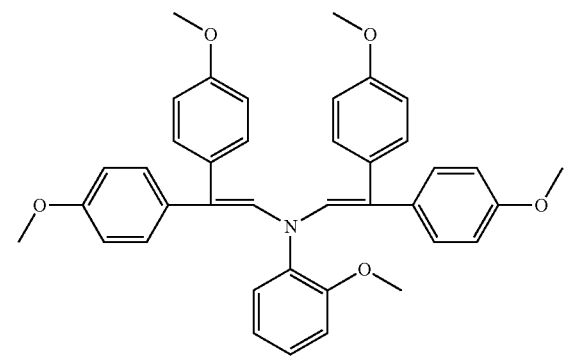
(37)
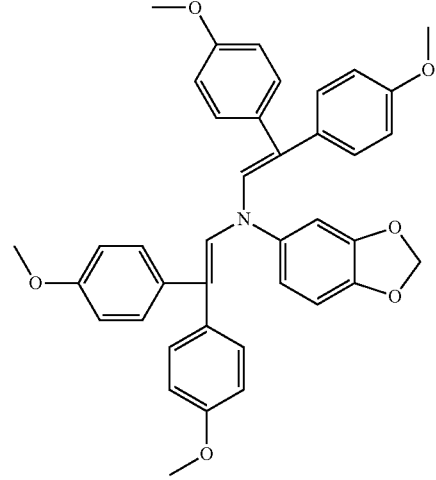
(38)
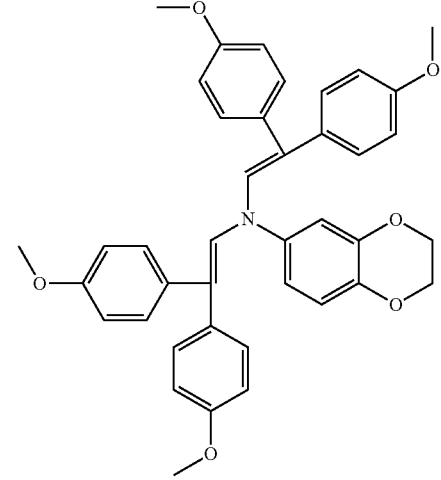
(39)

-continued
(40)
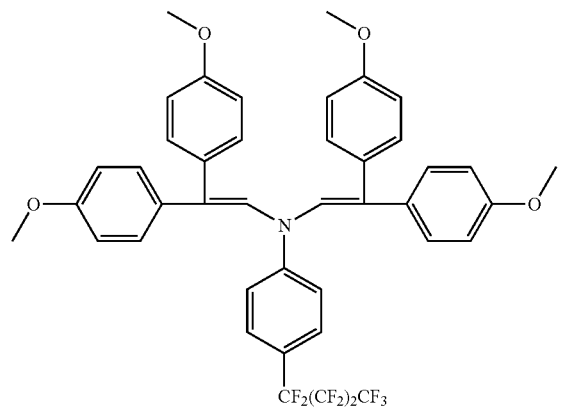
(41)
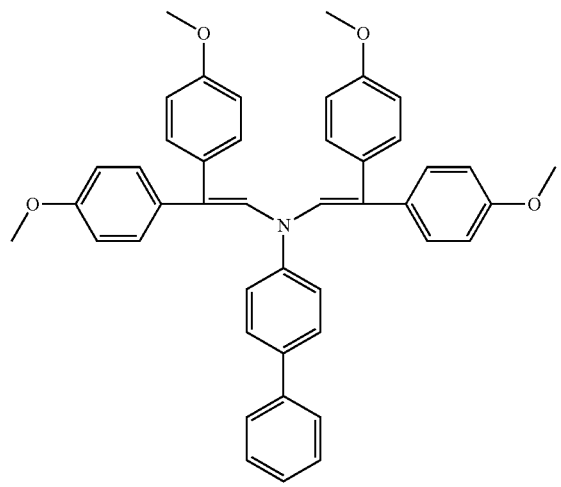
(42)
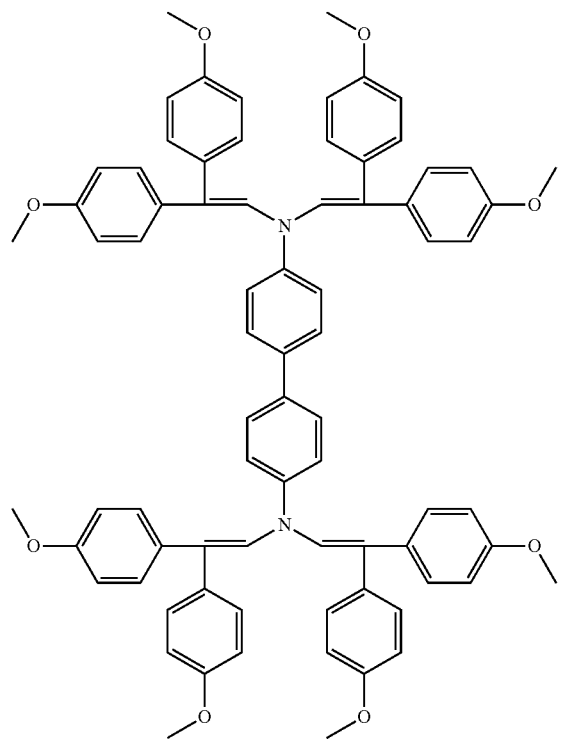
(43)
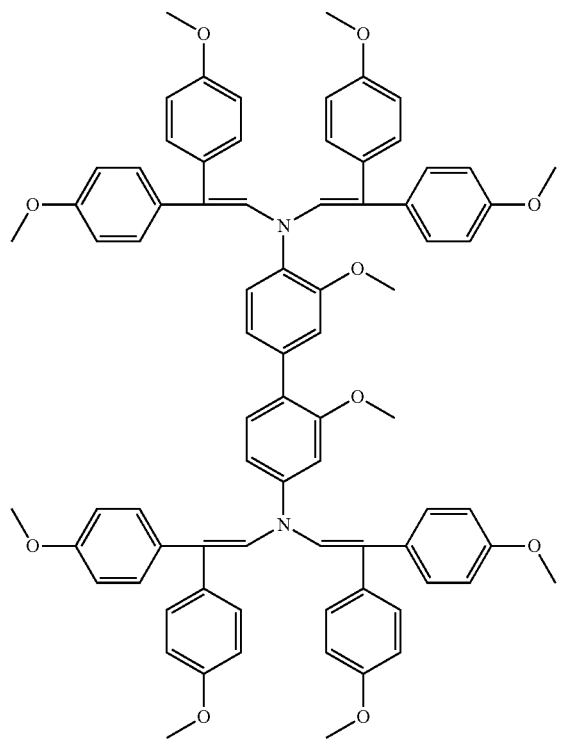

-continued
(44)
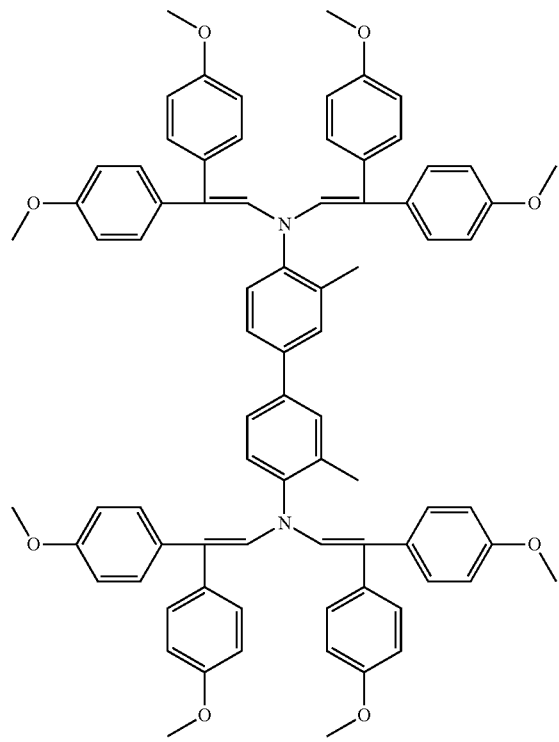
(45)
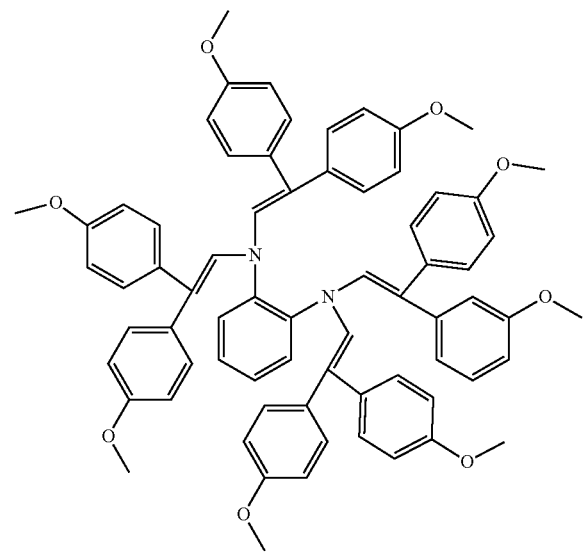
(46)
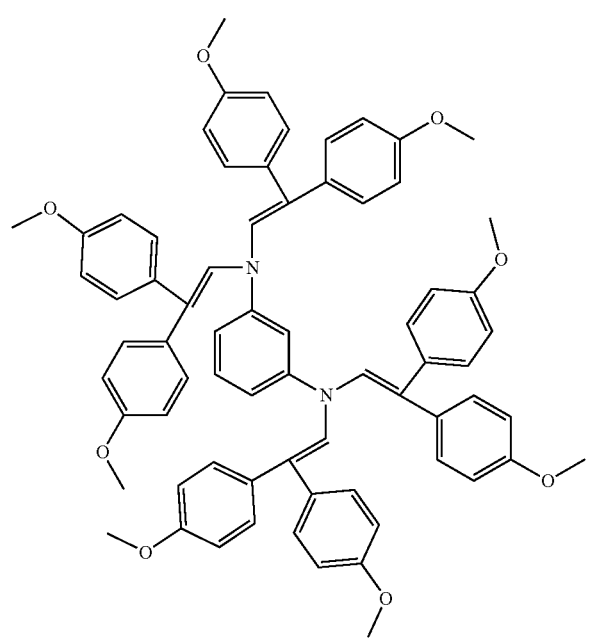
(47)
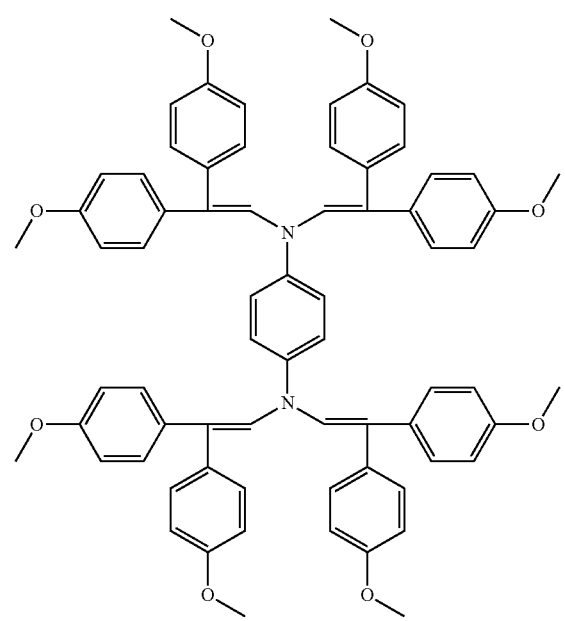

-continued
(48)
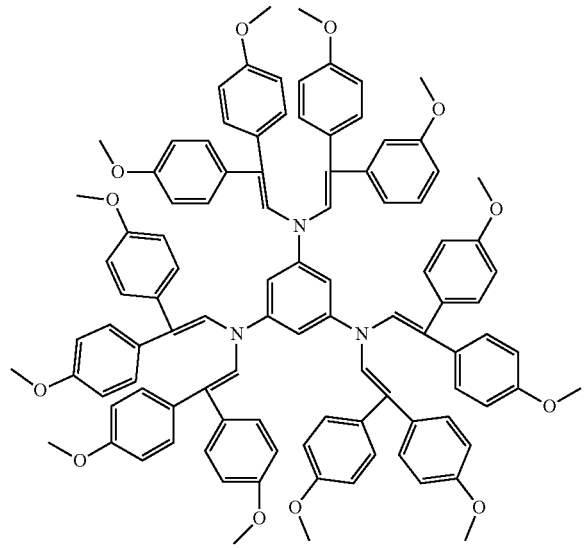
(49)
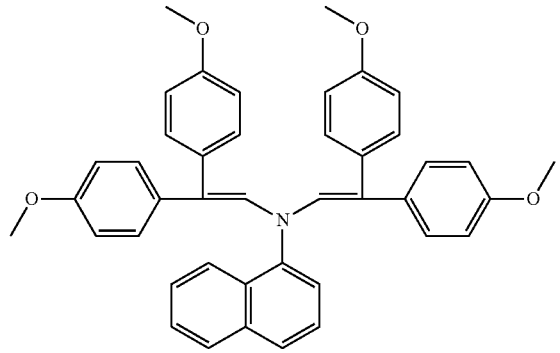
(50)
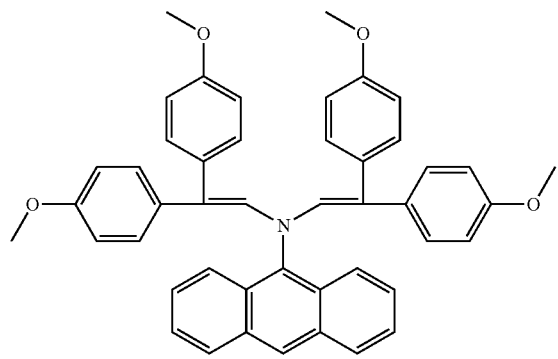
(51)
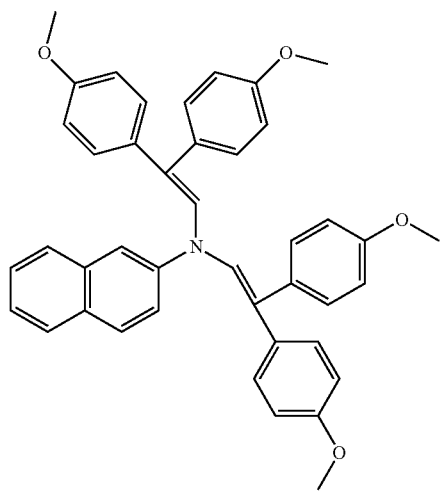
(52)
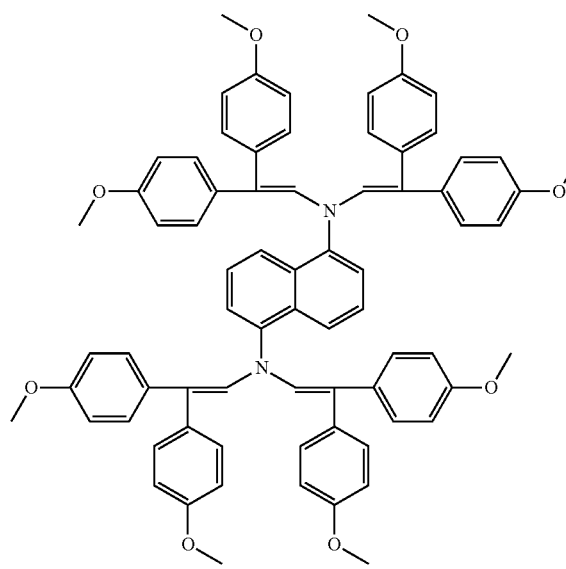
(53)
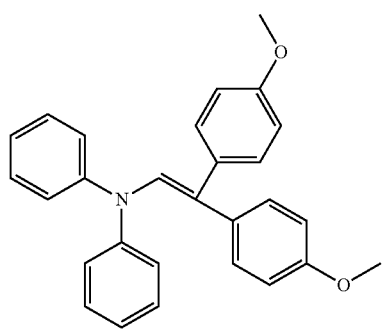

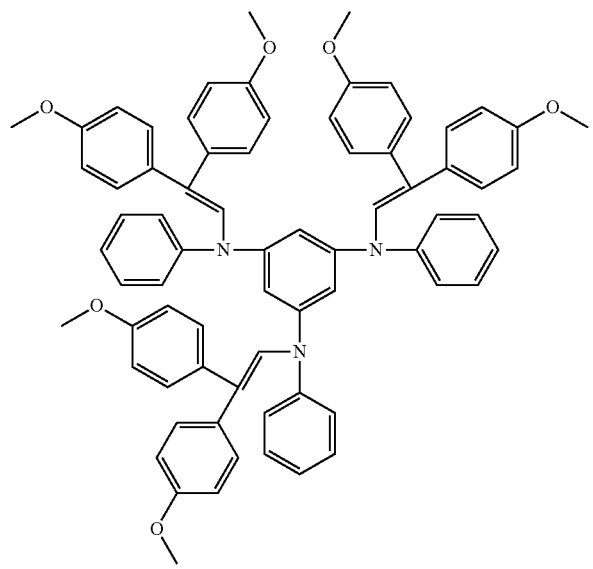

(54)

In a further aspect, the invention provides a hole transporting material comprising at least one molecule with hole transporting properties and combination of two or more of the aforementioned being selected from a compound of formula (I). Said compounds of the general formula (I) are for use as an organic non-polymeric semiconductor.

More specifically, the invention provides hole transporting material selected from at east one compound of the general formula (I).

The invention also provides in a further aspect an optoelectronic and/or photoelectrochemical device comprising a compound of the invention of formula (I).

The optoelectronic and/or photoelectrochemical device of the invention comprises a hole transporting material, wherein said hole transporting material comprises a compound of formula (I).

The optoelectronic and/or photoelectrochemical device of the invention is selected from an organic photovoltaic device, a photovoltaic solid state device, an p-n heterojunction, an organic solar cell, a dye sensitized solar cell, a solid state solar cell, a phototransistor, LED (light-emitting diode) or OLED (organic light-emitting diode).

According to an embodiment, the optoelectronic and/or photoelectrochemical device of the invention, in particular a photovoltaic solid state device comprises a conducting support layer, a surface-increasing scaffold structure, a sensitizer or sensitizer layer, a hole transporting layer and a counter electrode and/or metal layer.

In a further embodiment, the optoelectronic and/or photoelectrochemical device of the invention is a photovoltaic solid state device being a solid state solar cell comprising an organic-inorganic perovskite as sensitizer under the form of a layer.

According to an embodiment, the optoelectronic and/or photoelectrochemical device of the invention is a solar cell selected from an organic solar cell, a dye sensitized solar cell or a solid state device.

In an embodiment, the hole transporting layer of the optoelectronic and/or photoelectrochemical device, in particular a photovoltaic solid state device, is made of a hole transporting material of the invention comprising at least one small molecule hole transporting material being selected from a compound of formula (I). In particular the hole transporting material comprises at least one compound of formula (I).

According to another embodiment, the optoelectronic and/or photoelectrochemical device, in particular a photovoltaic solid state device, comprises a hole collector layer comprising a hole transporting material of the invention, a conductive layer, an electron blocking layer, a sensitizer layer and a current collector layer, wherein the hole collector layer is coated by the conductive layer; wherein the electron blocking layer is between the conductive layer and the sensitizer layer, which is in contact with the current collector layer being a metal or a conductor. According to a further embodiment, the conductive material is selected from one or more conductive polymers or one or more hole transporting materials, which may be selected from poly(3,4-ethylenedioxythiophene):poly(styrenesulfonate) (PEDOT:PSS), poly(3,4-ethylenedioxythiophene):poly(styrenesulfonate):grapheme nanocomposite (PEDOT:PSS:graphene), poly(N-vinylcarbazole) (PVK) and sulfonated poly(diphenylamine) (SPDPA), preferably from PEDOT:PSS, PEDOT:PSS:graphene and PVK, more preferably from PEDOT:PSS. Conductive polymers may also be selected from polymers comprising polyaniline, polypyrrole, polythiophene, polybenzene, polyethylenedioxythiophene, polypropylenedioxythiophene, polyacetylene, and combinations of two or more of the aforementioned, for example.

The conducting support layer is preferably substantially transparent. "Transparent" means transparent to at least a part, preferably a major part of the visible light. Preferably, the conducting support layer is substantially transparent to all wavelengths or types of visible light. Furthermore, the conducting support layer may be transparent to non-visible light, such as UV and IR radiation, for example.

The conducting support layer preferably functions and/or comprises a current collector, collecting the current obtained from the photovoltaic solid state device. The conducting support layer may comprise a material selected from indium doped tin oxide (ITO), fluorine doped tinoxide (FTO), $ZnO$—$Ga_2O_3$, $ZnO$—$Al_2O_3$, tin-oxide, antimony doped tin oxide (ATO), $SrGeO_3$ and zinc oxide, preferably coated on a transparent substrate, such as plastic or glass.

In this case, the plastic or glass provides the support structure of the layer and the cited conducting material provides the conductivity. Such support layers are generally known as conductive glass and conductive plastic, respectively, which are thus preferred conducting support layers in accordance with the invention. According to an embodiment, the conducting support layer comprises a conducting transparent layer, which may be selected from conducting glass and from conducting plastic.

According to an embodiment of the solar cell and the heterojunction of the invention, the surface-increasing scaffold structure is nanostructured and/or nanoporous. The scaffold structure is thus preferably structured on a nanoscale. The structures of said scaffold structure increase the effective surface compared to the surface of the conductive support.

According to an embodiment, said scaffold structure is made from and/or comprises a metal oxide. For example, the material of the scaffold structure is selected from semiconducting materials, such as Si, $TiO_2$, $SnO_2$, $Fe_2O_3$, ZnO, $WO_3$, $Nb_2O_5$, CdS, ZnS, PbS, $Bi_2S_3$, CdSe, CdTe, $SrTiO_3$, GaP, InP, GaAs, $CuInS_2$, $CuInSe_2$, and combinations thereof, for example.

According to an embodiment, the sensitizer layer of the photovoltaic solid state device comprising at least one pigment being selecting from organic, inorganic, organometallic and organic-inorganic pigments or a combination thereof. The sensitizer is preferably a light absorbing compound or material. Preferably, the sensitizer is a pigment, and most preferably the sensitizer is an organic-inorganic pigment.

The sensitizer layer may comprise one or more pigments of the group consisting of organometallic sensitizing compounds (telocyanine derived compounds, porphyrine derived compounds), metal free organic sensitizing compounds (diketopyrrolopyrrole (DPP) based sensitizer), inorganic sensitizing compounds such as quantum dots, $Sb_2S_3$ (Antimonysulfide, for example in the form of thin films), aggregates of organic pigments, nanocomposites, in particular organic-inorganic perovskites, and combinations of the aforementioned. For the purpose of the invention, it is in principle possible to use any type of dyes or sensitizer, including combinations of different types of dyes or different dyes of the same type.

According to an embodiment, the sensitizer layer of the photovoltaic solid state device of the invention is coated by a layer comprising a compound of formula (I). Preferably said sensitizer layer comprises an organic-inorganic perovskite.

According to an embodiment, the sensitizer or the sensitizer layer comprises, consists of or is made of an organic-inorganic perovskite. Said organic-inorganic perovskite is provided under a film of one perovskite pigment or mixed perovskite pigments or perovskite pigments mixed with further dyes or sensitizers.

According to a further embodiment, the sensitizer layer comprises a further pigment in addition to the organic-inorganic perovskite pigment, said further pigment selected from organic pigment, organometallic pigment or inorganic pigment.

According to another embodiment, the optoelectronic and/or photoelectrochemical device of the invention is a dye sensitized solar cell (DSC) comprising a compound of formula (I) as hole transporting material and a pigment as sensitizer selected from organic pigment, organometallic pigment or inorganic pigment or a combination thereof, as defined below. Organometallic sensitizers (dye or pigment) are disclosed, for example, in EP0613466, EP0758337, EP0983282, EP1622178, WO 2006/038823, WO 2009/107100, WO 2010/055471, WO 2011/039715 and porphyrin based compounds in PCT/IB2014/066581 and in European patent application no. EP13197269.7. Exemplary organic dyes (or pigment) are those disclosed in WO2009/098643, EP1990373, WO 2007/100033 for example. An organic dye was also used in European patent application no. EP 11161954.0 and in PCT/IB2011/054628. Metal free organic sensitizers (pigment or dye) such as DPP based compounds are disclosed in PCT/IB2013/056648 and in European patent application no. EP12182817.2.

The term "perovskite", for the purpose of this specification, refers to the "perovskite structure" and not specifically to the perovskite material, $CaTiO_3$. For the purpose of this specification, "perovskite" encompasses and preferably relates to any material that has the same type of crystal structure as calcium titanium oxide and of materials in which the bivalent cation is replaced by two separate monovalent cations. The perovskite structure has the general stoichiometry $AMX_3$, where "A" and "M" are cations and "X" is an anion. The "A" and "M" cations can have a variety of charges and in the original Perovskite mineral ($CaTiO_3$), the A cation is divalent and the M cation is tetravalent.

In a further embodiment of the optoelectronic and/or photoelectrochemical device of the invention, the organic-inorganic perovskite layer material comprises a perovskite-structure of formula (II):

$$AMX_3 \quad\quad (II)$$

wherein

A is an alkali metal ion, preferably $Li^+$, $Na^+$, $K^+$, $Rb^+$, $Cs^+$; ammonium or formamidium ion, wherein one or more hydrogens are substituted by alkyl or acyl group. Said ammonium ions, including mono, di, tri and tetra alkyl ammonium ions, wherein one or more hydrogens are substituted by alkyl group. Preferably, the substituent is alkyl group or groups independently selected from C1-C6, preferably methyl or ethyl groups. Said ammonium ions, including amidinium, N-alkyl amidinium and imidinium ions, wherein one or more hydrogens are substituted by alkyl group. Preferably, the amidinium or imidinium ions are selected from C1-C6 carboxamide groups, preferably formamidium or acetamidium groups. The hydrogen atoms in the organic cations A may be substituted by halogens selected from F, Cl, I and Br, preferably F or Cl. Preferably, A is $Cs^+$ or methyl ammonium ion ($MA^+$), or formamidium ion ($FA_+$).

M is a divalent metal cation selected from the group consisting of $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, $Eu^{2+}$, or $Yb^{2+}$; preferably $Pb^{2+}$, $Sn^{2+}$.

X is monovalent anion, independently selected from the group consisting of $Cl^-$, $Br^-$, $I^-$, $NCS^-$, $CN^-$, and $NCO^-$; preferably $Cl^-$, $Br^-$, $I^-$. X may be the same or different.

According to preferred embodiment, the examples of organic-inorganic perovskites are: methyl ammonium lead halides, for example, methylamonium lead iodide ($CH_3NH_3PbI_3$); methylamonium lead mixed halides, for example, $CH_3NH_3PbCl_2I$; formamidium lead halides, for example, $HC(NH_2)_2PbI_3$, $HC(NH_2)_2PbBr_3$ or $HC(NH_2)_2PbCl_2I$; cesium lead iodide ($CsPbI_3$), cesium tin iodide ($CsSnI_3$).

In a further embodiment of the optoelectronic and/or photoelectrochemical device of the invention, the organic-inorganic perovskite layer material comprises a mixed perovskite-structure, wherein A is the mixture of two or more cations as defined above, X is the mixture of two or more anions as defined above. Preferably, A is the mixture of two cations, M is Pb and X is the mixture of two anions. The formula (II) may be expressed as formula (III) below:

$$A^1{}_{1-y}A^2{}_yPbX^1{}_{3-z}X^2{}_z \quad (III)$$

wherein:

$A^1$ ir $A^2$ are organic monovalent cations as defined above for A;

$X^1$ ir $X^2$ may be the same or different monovalent anions selected from the group consisting of $Cl^-$, $Br^-$, $I^-$, $NCS^-$, $CN^-$ and $NCO^-$;

y is in the interval between 0.1 and 0.9;

z is in the interval between 0.2 and 2.

DETAILED DESCRIPTION OF THE INVENTION

General Synthesis Scheme of Compounds of General Formula (I).

Figure 1:
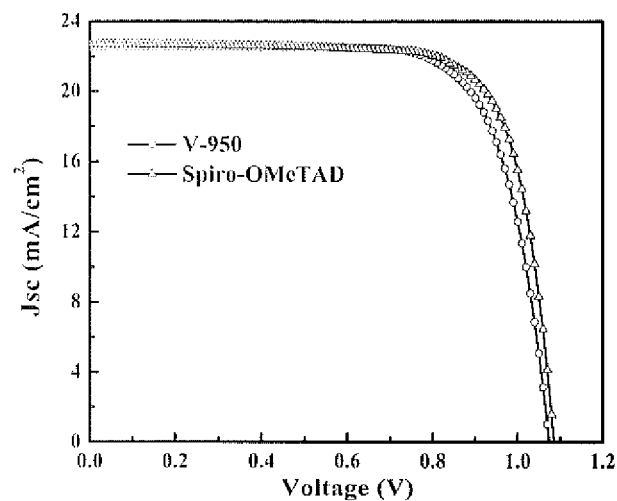
FIG. 1 shows the Current-Voltage curve of solar cells where compound (1) corresponding to compound V-950 and Spiro-OMeTAD are explored as hole transporting materials.

Hole transporting compounds containing enamine groups (—N—C═C) corresponding to the general formula (I) were synthesized via condensation reaction between 2,2-bis(4-methoxyphenyl)acetaldehyde (T. Kodera, K. Torizuka (Mitsubishi Paper Mills, Ltd.), Jpn. Kokai Tokkyo Koho JP 11043458, 1999) and primary, 3-amino-9-ethyl-9H-carbazole (Sigma-Aldrich), for example, or secondary amine of heterocycle in the presence of the catalyst (+/−) 10-camphorsulfonic acid (CSA) at reflux of toluene (FIG. 1). Dean-Stark apparatus is used to shorten reaction time and this is the main difference of the above mentioned method from the one described in the literature (Synthetic Metals, Vol. 158, 2008, 993). Compounds 1-5 were synthesized according to this method (Scheme 1):

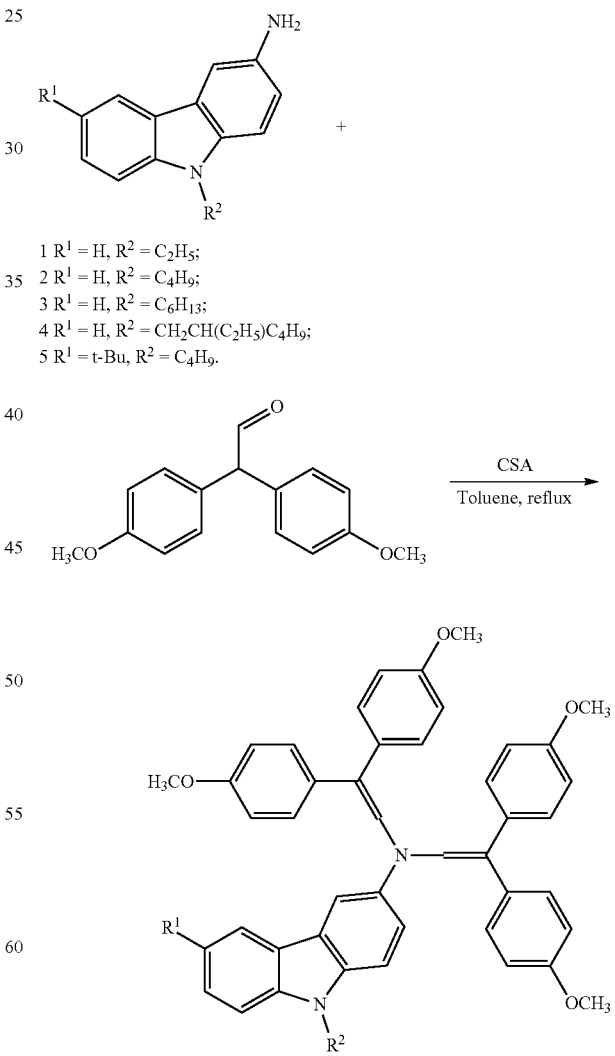

Hole transporting compound 6 containing enamine groups and corresponding to the general formula (I) was synthesized via condensation between 2,2-bis(4-methoxyphenyl)acetaldehyde and aromatic amine, 4-aminotriphenylamine (TCI Europe N.V.), for example, in the presence of the catalyst (+/−)10-camphorsulfonic acid (CSA) and using Dean-Stark apparatus (Scheme 2):

Scheme 2. Synthesis route to the hole transporting material 6

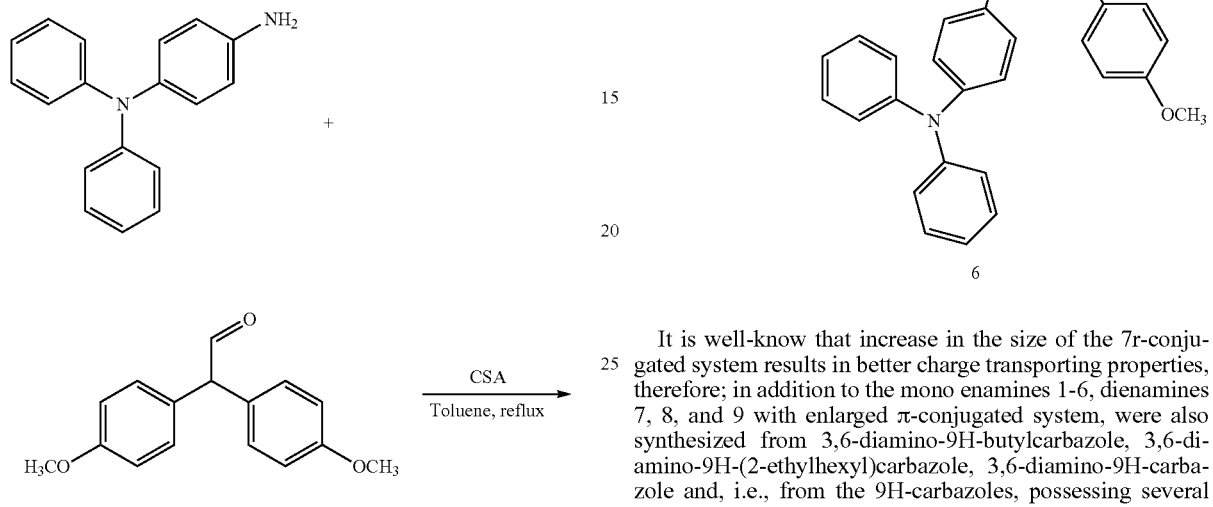

It is well-know that increase in the size of the π-conjugated system results in better charge transporting properties, therefore; in addition to the mono enamines 1-6, dienamines 7, 8, and 9 with enlarged π-conjugated system, were also synthesized from 3,6-diamino-9H-butylcarbazole, 3,6-diamino-9H-(2-ethylhexyl)carbazole, 3,6-diamino-9H-carbazole and, i.e., from the 9H-carbazoles, possessing several amino groups Scheme 3).

Scheme 3. Synthesis route to the hole transporting materials 7, 8, and 9

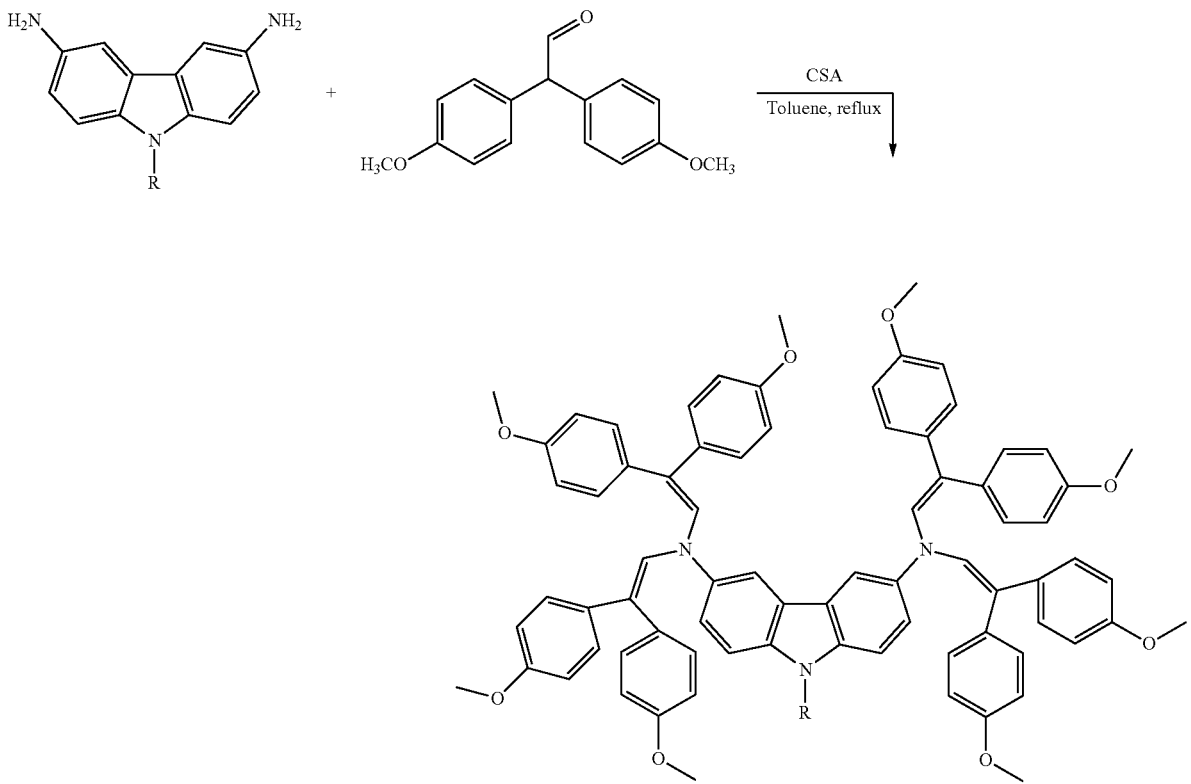

7 R = C$_6$H$_{13}$,
8 R = CH$_2$CH(C$_2$H$_5$)C$_4$H$_9$.
9 R = 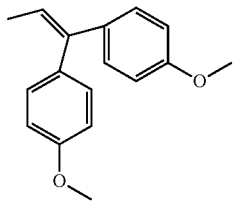

-continued

Hole transporting fluorene-based compounds 10-14 containing enamine groups and corresponding to the general formula (I) were synthesized using straightforward chemistry with excellent yields and high purity. As shown in Scheme 4, hole transporting material 10 only required one-pot reaction condensing inexpensive commercially available 2,7-diaminofluorene (TC Europe N.V.) and 2,2-bis(4-methoxyphenyl)acetaldehyde in the presence of camphor sulfonic acid. Compound 10 was further reacted with different alkylating agents (RX) in the presence of interphase catalyst benzyltriethylammonium chloride (BTEAC) to yield methyl-, propyl-, hexyl-, and benzyl-substituted fluorene enamines as final HTMs 11, 12, 13, and 14, respectively.

Scheme 4. Synthesis route to the hole transporting materials 10-14

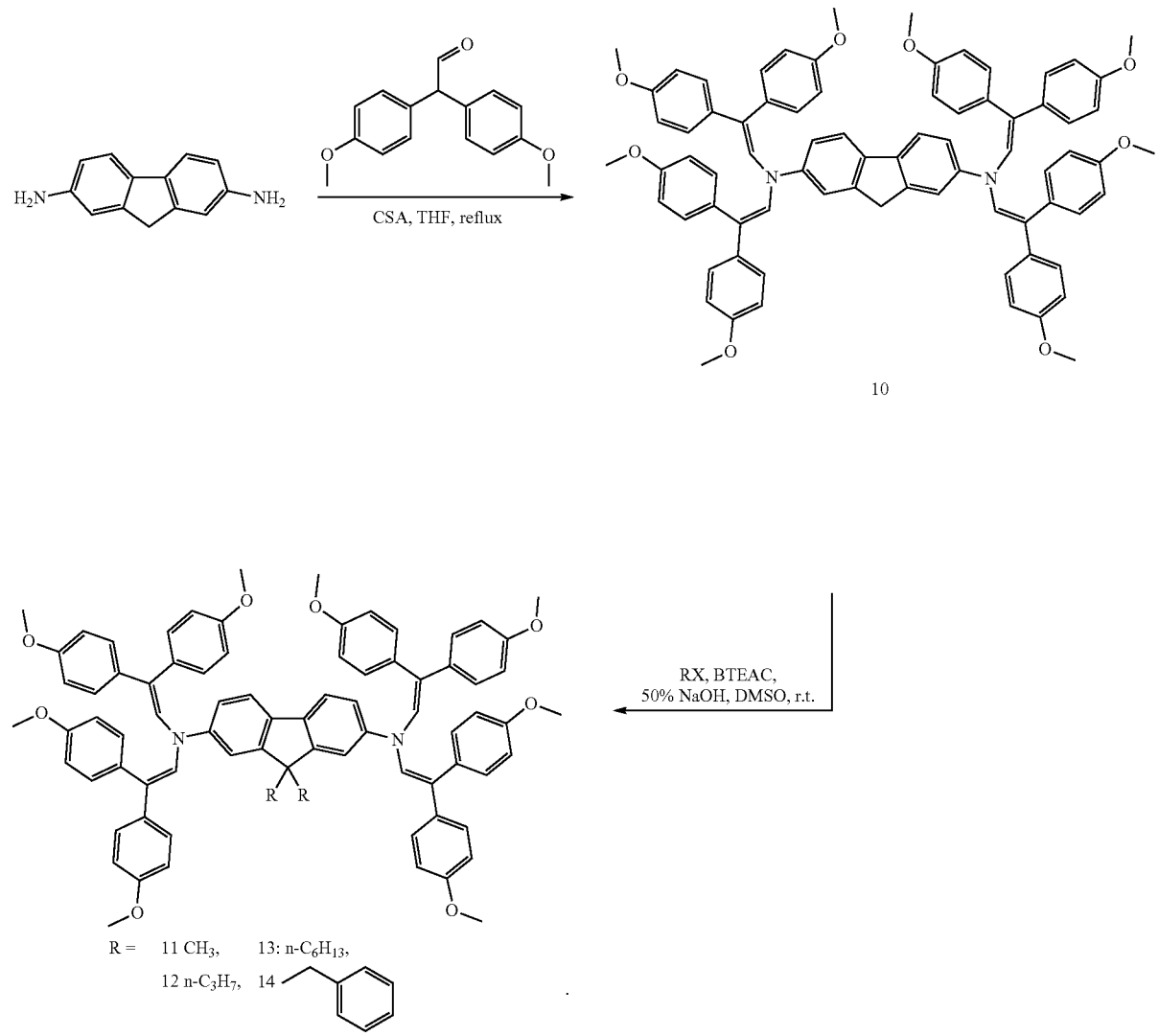

Hole transporting spirofluorene-based compounds 15-18 containing enamine groups and corresponding to the general formula (I) were synthesized in one-pot reaction condensing commercially available 9,9'-spirobi[9H-fluoren]-2-amine (TC Europe N.V.), 9,9'-spirobi[fluorene]-2,7-diamine (Fluorochem Ltd), 2,2',7,7'-tetraamino-9,9'-spirobifluorene (ABClabtory Scientific Co., Ltd.), and 9,9'-spirobi[fluorene]-2,7-diamine with (2,2-bis(4-methoxyphenyl)acetaldehyde in the presence of camphor sulfonic acid (Scheme 5).

Scheme 5. Synthesis route to the hole transporting materials 15-18

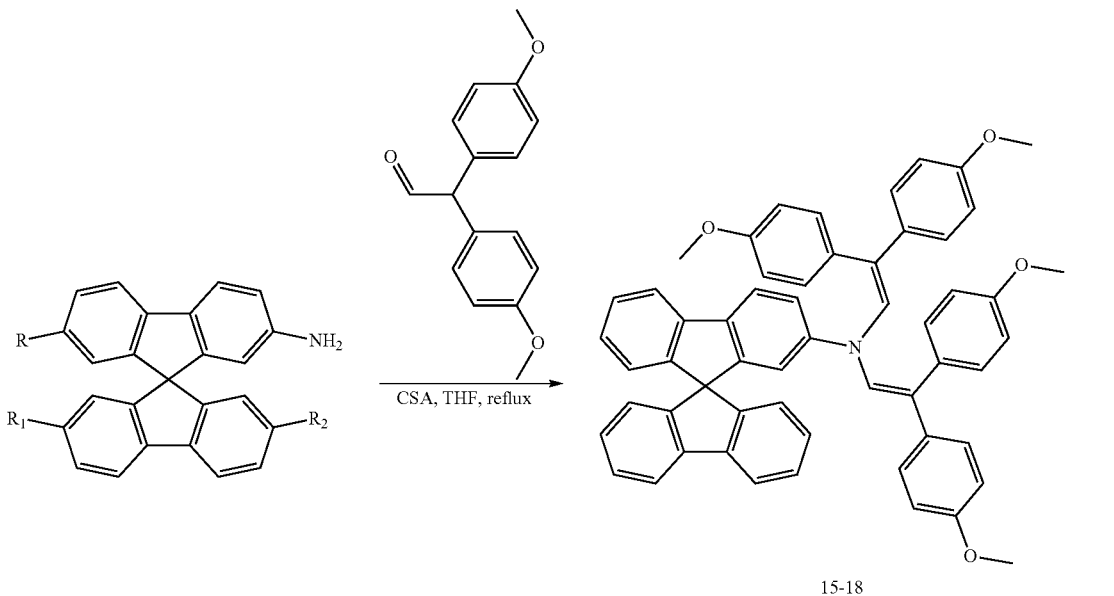

15 R = $R_1$ = $R_2$ = H,

16 R = $R_2$ = H,
  $R_1$ =

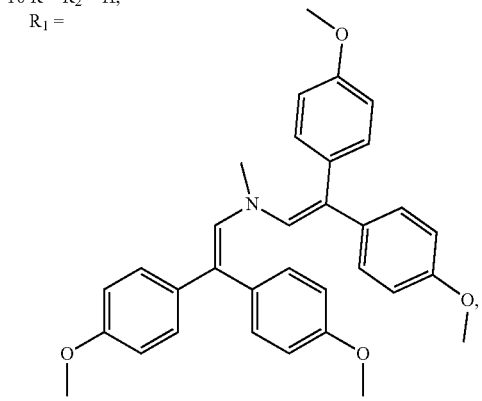

17 $R_1$ = $R_2$ = H,
  R =

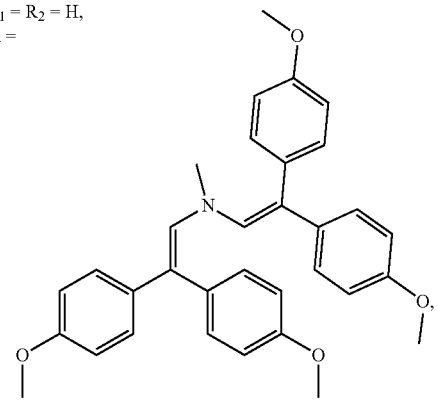

18 R = $R_1$ = $R_2$ =

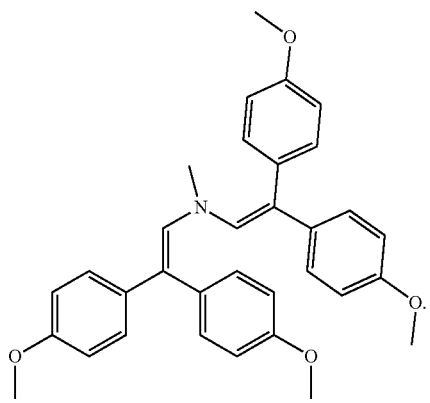

MODES FOR CARRYING OUT THE INVENTION

Information on examples of real embodiments is provided below, describing the modes of preparation compounds (1-18) of present invention and properties thereof. This information is provided for the illustrative purpose and is not limiting the scope of the present invention.

Example 1

9-ethyl-3-{N,N-bis[2,2-bis(4-methoxyphenyl)vinyl]amino}-9H-carbazole (see Scheme 1, Compound I or V-950)

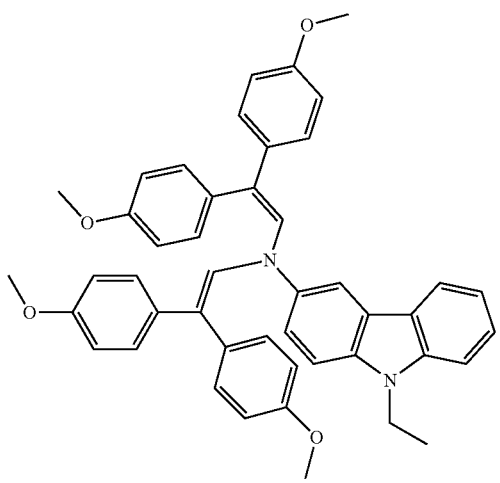 [SMILES: CCn1c2ccccc2c2cc(N(C=C(c3ccc(OC)cc3)c3ccc(OC)cc3)C=C(c3ccc(OC)cc3)c3ccc(OC)cc3)ccc21]

3-amino-9-ethylcarbazole (250 mg, 1.19 mmol) is dissolved in toluene (5 ml+volume of Dean-Stark apparatus), (+/−)10-camphorsulfonic acid (276 mg, 1.19 mmol) was added and reaction mixture was refluxed for 20 min. Then 2,2-bis(4-methoxyphenyl)acetaldehyde (915 mg, 3.57 mmol) was added and reaction was continued using Dean-Stark apparatus for another 2 hours. After reaction was finished (TLC, acetone:n-hexane/v:v, 1:4) reaction mixture was extracted with ethyl acetate, organic layer dried with anhydrous $Na_2SO_4$, filtered and organic solvents removed in vacuum. The residue was dissolved in warm ethanol; formed crystals were filtered, washed with cold ethanol and recrystallized from the mixture of toluene:ethanol (1:2). Obtained crystals were dried under vacuum at 40° C. to yield 1 as yellow crystals (590 mg, 64 10%); m.p. 226-228° C.

$^1$H NMR (700 MHz, DMSO-$d_6$, δ): 8.15 (d, J=7.8 Hz, 1H, 5-H, Ht), 7.80 (s, 1H, 4-H, Ht), 7.58-7.54 (m, 2H, 1,2-H, Ht), 7.44-7.40 (m, 1H 6-H, Ht), 7.24 (d, J=7.0 Hz, 1H, 8-H, Ht), 7.11-7.08 (m, 1H, 7-H, Ht), 6.96 (d, J=8.8 Hz, 4H, p-Ph), 6.88 (d, J=9.0 Hz, 4H, p-Ph), 6.67 (d, J=9.0 Hz, 4H, p-Ph), 6.44 (d, J=8.8 Hz, 4H, p-Ph), 5.79 (s, 2H, NCH), 4.42 (kv, J=7.0 Hz, 2H, NCH$_2$), 3.79 (s, 6H, OCH$_3$), 3.70 (s, 6H, OCH$_3$), 1.31 (t, J=7.0 Hz, 3H, CH$_3$).

$^{13}$C NMR (176 MHz, DMSO-$d_6$ 6): 159.1, 139.1, 136.4, 134.5, 132.6, 132.3, 130.7, 129.3, 128.7, 127.6, 126.3, 123.43, 122.33, 121.37, 118.76, 117.16, 114.35, 114.24, 113.53, 110.14, 109.47, 108.72, 55.1 (OCH$_3$), 55.51 (OCH$_3$), 37.46 (CH$_2$), 14.15 (CH$_3$).

Elemental analysis: Calculated, %: C, 80.44; H, 6.16; N, 4.08. $C_{46}H_{42}N_2O_4$. Found, %: C, 80.17; H, 6.02; N, 3.91.

Example 2

9-butyl-3-{N,N-bis[2,2-bis(4-methoxyphenyl)vinyl]amino}-9H-carbazole (see Scheme 1, Compound 2 or V-1013)

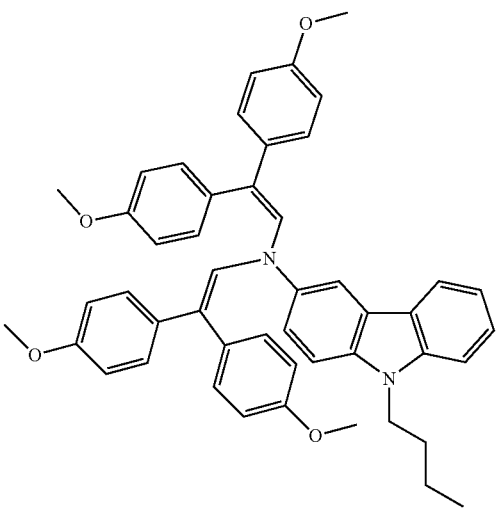 [SMILES: CCCCn1c2ccccc2c2cc(N(C=C(c3ccc(OC)cc3)c3ccc(OC)cc3)C=C(c3ccc(OC)cc3)c3ccc(OC)cc3)ccc21]

3-amino-9-butylcarbazole (1 g, 4.2 mmol) is dissolved in toluene (18 ml), (+/−)10-camphorsulfonic acid (1 g, 4.3 mmol) was added and reaction mixture was refluxed for 20 min. Then 2,2-bis(4-methoxyphenyl)acetaldehyde (2.69 g, 10.5 mmol) was added and reaction was continued using Dean-Stark apparatus for another 1 hour. After reaction was finished (TLC, acetone:n-hexane/v:v, 1:4) reaction mixture was extracted with ethyl acetate, organic layer dried with anhydrous $Na_2SO_4$, filtered and organic solvents removed in vacuum. The residue was purified by column chromatography using THF: n-hexane/v:v, 1:49 and recrystallized from ethanol. Obtained crystals were dried under vacuum at 40° C. to yield 2 as yellow crystals (1.65 g, 55%).

$^1$H NMR (400 MHz, CDCl$_3$ δ): 8.05 (d, J=8.9 Hz, 1H, 5-H, Ht), 7.81 (s, 1H, 4-H, Ht), 7.44 (t, J=7.2 Hz, 1H, 6-H, Ht), 7.39-7.33 (m, 1H, 8-H, Ht), 7.33 (t, J=7.5 Hz, 2H, 1,2-H, Ht), 7.17 (t, J=7.4 Hz, 1H, 7-H, Ht), 7.07 (d, J=8.7 Hz, 4H, p-Ph), 6.83 (d, J=8.7 Hz, 4H, p-Ph), 6.67 (d, J=8.7 Hz, 8 Hz, 4H, p-Ph), 6.54 (d, J=8.7 Hz, 4H, p-Ph), 5.89 (s, 2H, NCH), 4.30 (t, J=7.2 Hz, 2H, NCH$_2$), 3.85 (s, 6H, OCH$_3$), 3.77 (s, 6H, OCH$_3$), 1.88-1.82 (m, 2H, NCH$_2$), 1.55 (s, 2H, NCH$_2$CH$_2$), 1.44-1.39 (m, 2H, NCH$_2$CH$_2$CH$_2$), 0.96 (t, J=7.2 Hz, 3H, CH$_3$).

$^{13}$C NMR (75 MHz, CDCl$_3$ δ): 159.0, 158.7, 141.2, 139.2, 136.9, 134.9, 133.2, 130.8, 129.8, 128.9, 127.9, 125.9, 123.7, 122.6, 120.9, 118.5, 116.9, 114.6, 114, 113.2, 109.1, 108.8, 55.6 (OCH$_3$), 55.4 (OCH$_3$), 43.1 (CH$_2$), 31.4 (CH$_2$), 20.7 (CH$_2$), 14.1 (CH$_3$).

Elemental analysis: Calculated, %: C, 80.64; H, 6.49; N, 3.92. $C_{48}H_{46}N_2O_4$. Found, %: C, 80.44; H, 6.29; N, 3.72.

Example 3

9-hexyl-3-{N,N-bis[2,2-bis(4-methoxyphenyl)vinyl]amino}-9H-carbazole (see Scheme 1, Compound 3 or V-1001)

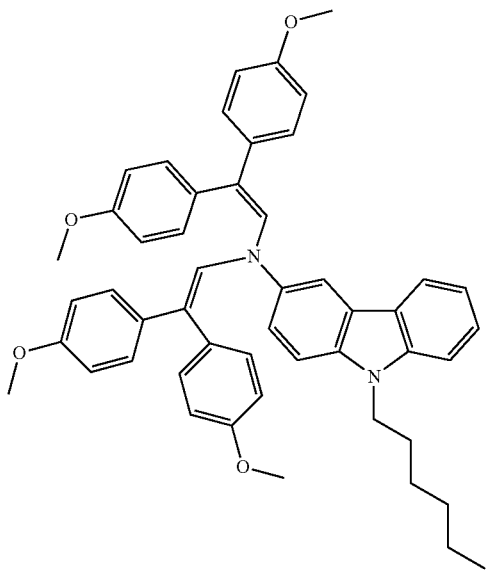 [SMILES: CCCCCCn1c2ccccc2c2cc(N(C=C(c3ccc(OC)cc3)c3ccc(OC)cc3)C=C(c3ccc(OC)cc3)c3ccc(OC)cc3)ccc21]

3-amino-9-hexylcarbazole (1 g, 3.8 mmol) is dissolved in toluene (18 ml), (+/−)10-camphorsulfonic acid (1 g, 4.3 mmol) was added and reaction mixture was refluxed for 20 min. Then 2,2-bis(4-methoxyphenyl)acetaldehyde (2.41 g, 9.4 mmol) was added and reaction was continued using Dean-Stark apparatus for another 1 hour. After reaction was finished (TLC, acetone:n-hexane/v:v, 1:4) reaction mixture was extracted with ethyl acetate, organic layer dried with anhydrous $Na_2SO_4$, filtered and organic solvents removed in vacuum. The residue was purified by column chromatography using acetone: n-hexane/v:v, 1:49 and recrystallized from ethanol. Obtained crystals were dried under vacuum at 40° C. to yield 3 as yellow crystals (1.56 g, 55%).

$^1$H NMR (400 MHz, $CDCl_3$ δ): 8.07 (d, J=7.7 Hz, 1H, 5-H, Ht), 7.8 (s, 1H, 4-H, Ht), 7.38 (d, 1H, J=8.2 Hz, 1H, 7-H, Ht), 7.33 (t, J=3.6 Hz, 2H, 6-H, Ht), 7.12-7.19 (m, 1H, 8-H, Ht), 7.07 (t, J=5.7 Hz, 4H, p-Ph), 6.84 (t, J=5.8 Hz, 4H, p-Ph), 6.65-6.68 (m, 4H, p-Ph), 6.53-6.56 (m, 4H, p-Ph), 5.89 (s, 2H, NCH), 4.8 (t, J=7.2 Hz, 2H, $NCH_2$), 3.84 (s, 6H, $OCH_3$), 3.77 (s, 6H, $OCH_3$), 1.85-1.89 (m, 2H, $NCH_2CH_2$), 1.37-1.41 (m, 2H, $NCH_2CH_2CH_2$), 1.29-1.33 (m, 4H, $NCH_2CH_2CH_2CH_2CH_2$), 0.88 (t, J=7.0 Hz, 3H, $CH_3$).

$^{13}$C NMR (100 MHz, $CDCl_3$ δ): 159.0, 158.7, 141.2, 139.2, 136.2, 134.9, 133.2, 130.8, 129.8, 128.9, 127.9, 125.9, 123.7, 122.6, 120.9, 118.6, 116.9, 114.6, 114.0, 113.2, 109.1, 108.7, 55.6 ($OCH_3$), 55.4 ($OCH_3$), 43.4 ($CH_2$), 31.8 ($CH_2$), 29.1 ($CH_2$), 27.1 ($CH_2$), 22.7 ($CH_2$), 14.2 ($CH_3$).

Elemental analysis: Calculated, %: C, 80.83; H, 6.78; N, 3.77. $C_{50}H_{50}N_2O_4$. Found, %: C, 80.63; H, 6.68; N, 3.57.

Example 4

9-(2-ethylhexyl)-3-{N,N-bis[2,2-bis(4-methoxyphenyl)vinyl]amino}-9H-carbazole (see Scheme 1, Compound 4 or V-1000)

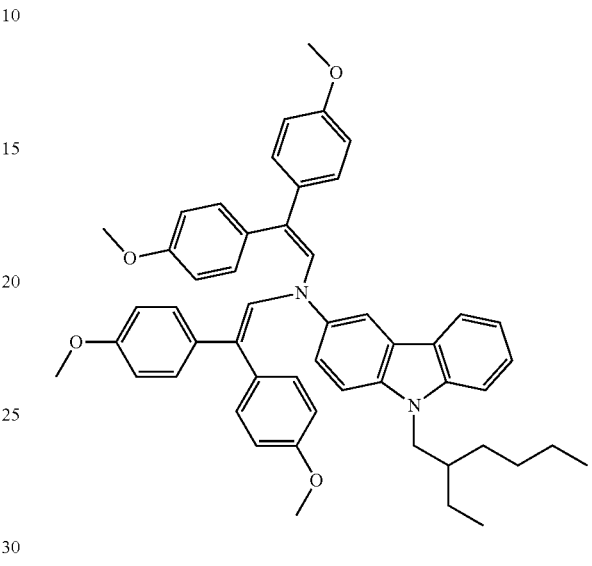

3-amino-9-(2-ethylhexyl)carbazole (1 g, 3.4 mmol) is dissolved in toluene (17 ml), (+/−) 10-camphorsulfonic acid (1 g, 4.3 mmol) was added and reaction mixture was refluxed for 20 min. Then 2,2-bis(4-methoxyphenyl)acetaldehyde (2.18 g, 8.5 mmol) was added and reaction was continued using Dean-Stark apparatus for another 1 hour. After reaction was finished (TLC, acetone:n-hexane/v:v, 1:4) reaction mixture was extracted with ethyl acetate, organic layer dried with anhydrous $Na_2SO_4$, filtered and organic solvents removed in vacuum. The residue was purified by column chromatography using acetone: n-hexane/v:v, 1:49 and recrystallized from ethanol. Obtained crystals were dried under vacuum at 40° C. to yield 4 as yellow crystals (1.45 g, 57%).

$^1$H NMR (400 MHz, $CDCl_3$ δ): 8.06 (d, J=7.8 Hz, 1H, 5-H, Ht), 7.81 (s, 1H, 4-H, Ht), 7.7 (t, J=7.7 Hz, 1H, 6-H, Ht), 7.36-7.34 (m, 1H, 8-H, Ht), 7.33-7.31 (m, 2H, 1,2-H, Ht), 7.17 (t, J=7.4 Hz, 1H, 7-H, Ht), 7.07 (d, J=8.4 Hz, 4H, p-Ph), 6.84 (d, J=8.4 Hz, 4H, p-Ph), 6.67 (d, J=8.4 Hz, 4H, p-Ph), 6.54 (d, J=8.4 Hz, 4H, p-Ph), 5.89 (s, 2H, NCH), 4.18-4.11 (m, 2H, $NCH_2$), 3.85 (s, 6H, $OCH_3$), 3.77 (s, 6H, $OCH_3$), 2.08-2.05 (m, 1H, $NCH_2CH$), 1.44-1.32 (m, 6H, $NCH_2(CH_2)3$), 1.32-1.27 (m, 2H, $NCH_2CHCH_2$), 0.93 (t, J=7.3 Hz, 3H, $CH_2CH_3$), 0.89 (t, J=7.3 Hz, 3H, $CH_2CH_3$).

$^{13}$C NMR (100 MHz, $CDCl_3$, δ): 159.0, 158.7, 141.7, 139.2, 137.4, 134.9, 133.2, 130.8, 129.8, 128.9, 127.9, 125.8, 123.6, 122.6, 120.9, 118.6, 116.9, 114.6, 114.0, 113.2, 109.4, 109.1, 108.7, 55.6 ($OCH_3$), 55.4 ($OCH_3$), 47.7 (CH), 39.7 ($CH_2$), 31.2 ($CH_2$), 29.0 ($CH_2$), 24.5 ($CH_2$), 23.2 ($CH_2$), 14.2 ($CH_3$), 11.1 ($CH_3$).

Elemental analysis: Calculated, %: C, 81.01; H, 7.06; N, 3.63. $C_{52}H_{54}N_2O_4$. Found, %: C, 80.81; H, 6.84; N, 3.43.

Example 5

9-butyl-6-(tert-butyl)-3-{N,N-[2,2-bis(4-methoxyphenyl)vinyl]amino}-9H-carbazole (see Scheme 1, Compound 5 or V-1004)

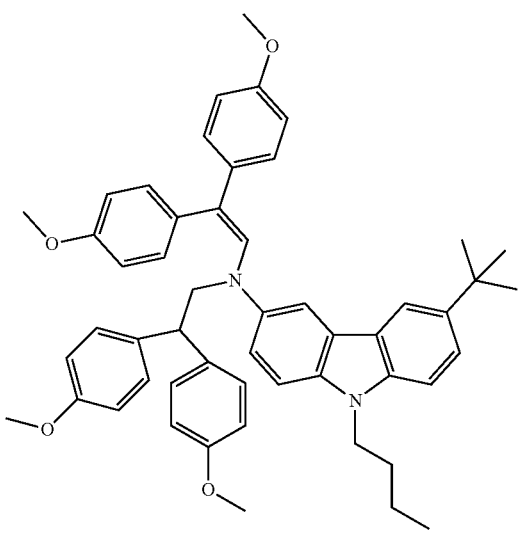 [SMILES: CCCCn1c2ccc(N(C=C(c3ccc(OC)cc3)c3ccc(OC)cc3)CC(c3ccc(OC)cc3)c3ccc(OC)cc3)cc2c2cc(C(C)(C)C)ccc21]

3-amino-6-(tert-butyl)-9-butylcarbazole (1 g, 3.4 mmol) is dissolved in toluene (17 ml), (+/−)10-camphorsulfonic acid (1 g, 4.3 mmol) was added and reaction mixture was refluxed for 20 min. Then 2,2-bis(4-methoxyphenyl)acetaldehyde (2.18 g, 8.5 mmol) was added and reaction was continued using Dean-Stark apparatus for another 30 min. After reaction was finished (TLC, acetone:n-hexane/v:v, 1:4) reaction mixture was extracted with ethyl acetate, organic layer dried with anhydrous $Na_2SO_4$, filtered and organic solvents removed in vacuum. The residue was purified by column chromatography using THF: n-hexane/v:v, 1:24 and precipitated from 20% solution in THF to 20-fold excess of methanol. Obtained material was dried under vacuum at 40° C. to yield 5 as yellow amorphous powder (1.45 g, 57%).

$^1$H NMR (400 MHz, $CDCl_3$ δ): 8.09 (d, J=1.7 Hz, 1H, 5-H, Ht), 7.81 (s, 1H, 4-H, Ht), 7.54-7.50 (m, 1H, 6-H, Ht), 7.33-7.27 (m, 3H, Ht), 7.26 (s, 1H, 7-H, Ht), 7.08 (d, J=8.8 Hz, 4H, p-Ph), 6.84 (d, J=8.8 Hz, 4H, p-Ph), 6.68 (d, J=8.8 Hz, 4H, p-Ph), 6.55 (d, J=8.8 Hz, 4H, p-Ph), 5.90 (s, 2H, NCH), 4.27 (t, J=7.0 Hz, 2H, $NCH_2$), 3.85 (s, 6H, $OCH_3$), 3.78 (s, 6H, $OCH_3$), 1.43 (s, 9H, $C(CH_3)3$), 1.47-1.39 (m, 2H, $CH_2$), 0.96 (t, J=7.3 Hz, 3H, $CH_3$).

$^{13}$C NMR (100 MHz, $CDCl_3$ δ): 159.0, 158.7, 141.7, 139.5, 139.4, 138.9, 137.4, 134.9, 133.2, 130.8, 129.6, 129.5, 128.9, 128.1, 123.8, 122.3, 117.2, 116.6, 114.0, 113.2, 109.0, 108.7, 108.2, 55.6 ($OCH_3$), 55.4 ($OCH_3$), 43.1 ($CH_2$), 34.9 ($CH_2$), 32.2 ($CH_2$), 31.5 ($CH_2$), 23.8 ($CH_3$), 20.8 ($CH_3$), 14.1 ($CH_3$).

Elemental analysis: Calculated, %: C, 81.01; H, 7.06; N, 3.63. $C_{52}H_{54}N_2O_4$. Found, %: C, 80.81; H, 6.86; N, 3.43.

Example 6

4-{N,N-bis[2,2-bis(4-methoxyphenyl)vinyl]amino}triphenylamine (see Scheme 2, Compound 6 or V-1012)

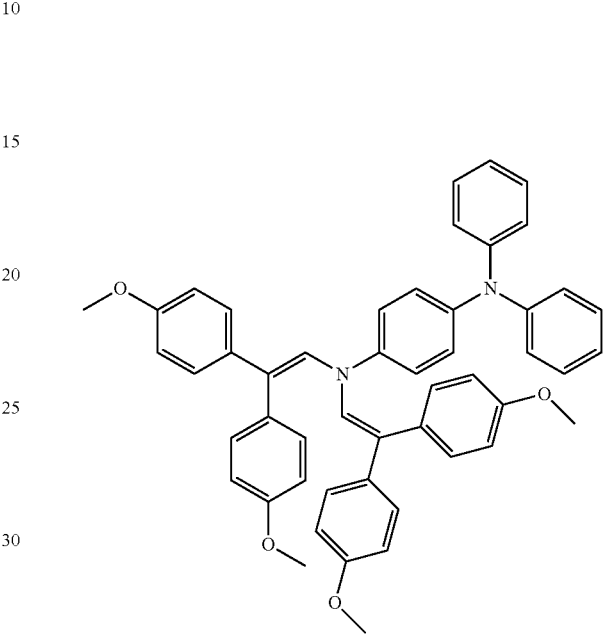

4-aminotriphenylamine (1 g, 3.8 mmol) is dissolved in toluene (18 ml), (+/−)10-camphorsulfonic acid (1 g, 4.3 mmol) was added and reaction mixture was refluxed for 20 min. Then 2,2-bis(4-methoxyphenyl)acetaldehyde (2.46 g, 9.6 mmol) was added and reaction was continued using Dean-Stark apparatus for another 30 min. After reaction was finished (TLC, THF:n-hexane/v:v, 1:4) reaction mixture was extracted with ethyl acetate, organic layer dried with anhydrous $Na_2SO_4$, filtered and organic solvents removed in vacuum. The residue was purified by column chromatography using THF: n-hexane/v:v, 1:24 and precipitated from 20% solution in THF to 20-fold excess of methanol. Obtained material was dried under vacuum at 40° C. to yield 6 as yellow amorphous powder (1.6 g, 58%).

$^1$H NMR (400 MHz, $CDCl_3$, 6): 7.31-7.22 (m, 4H, Ar), 7.15-6.93 (m, 14H, Ar), 6.88 (d, J=8.3 Hz, 4H, p-Ph), 6.67 (d, J=8.3 Hz, 4H, p-Ph), 6.53 (d, J=8.3 Hz, 4H, p-Ph), 5.83 (pl.s, 2H, NCH), 3.89 (s, 6H, $OCH_3$), 3.78 (s, 6H, $OCH_3$).

$^{13}$C NMR (100 MHz, $CDCl_3$, δ): 158.9, 158.6, 148.1, 141.8, 134.4, 132.7, 136.7, 130.2, 129.1, 128.8, 126.4, 123.2, 122.0, 117.9, 114.4, 113.8, 113.0, 99.9, 55.4 ($OCH_3$), 55.2 ($OCH_3$).

Elemental analysis: Calculated, %: C, 81.50; H, 6.02; N, 3.80. $C_{50}H_{44}N_2O_4$. Found, %: C, 81.20; H, 5.82; N, 3.48.

Example 7

9-butyl-3,6-bis{$N^3,N^3,N^6,N^6$-tetrakis(2,2-bis[4-methoxyphenyl)vinyl]amino}-9H-carbazole (see Scheme 3, Compound 7 or V-1020)

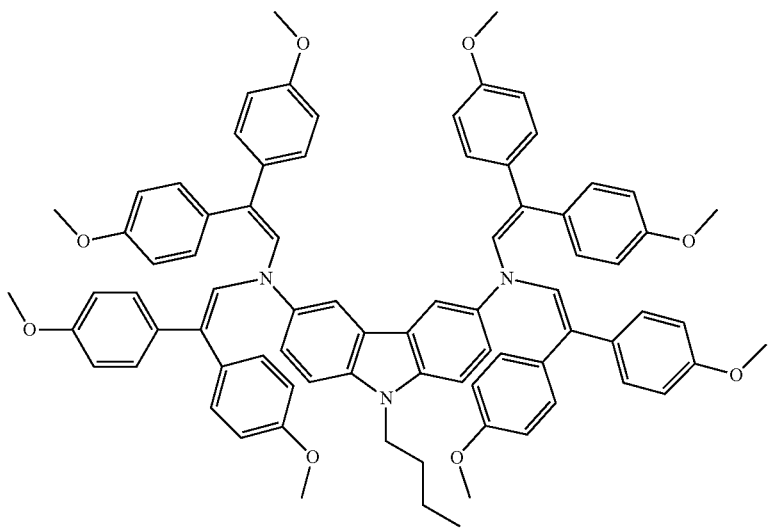

9-butylcarbazole-3,6-diamine (1 g, 4.8 mmol) is dissolved in toluene (21 ml), (+/−)10-camphorsulfonic acid (1 g, 4.3 mmol) was added and reaction mixture was refluxed for 20 min. Then 2,2-bis(4-methoxyphenyl)acetaldehyde (5.04 g, 19.7 mmol) was added and reaction was continued using Dean-Stark apparatus for another 1 h. After reaction was finished (TLC, acetone:n-hexane/v:v, 1:4) reaction mixture was extracted with ethyl acetate, organic layer dried with anhydrous $Na_2SO_4$, filtered and organic solvents removed in vacuum. The residue was purified by column chromatography using acetone: n-hexane/v:v, 3:22 and precipitated from 20% solution in THF to 20-fold excess of methanol. Obtained material was dried under vacuum at 40° C. to yield 7 as yellow amorphous powder (3.2 g, 55%).

$^1$H NMR (400 MHz, $CDCl_3$ δ): 7.76 (s, 2H, 4,5-H, Ht), 7.35-7.26 (m, 4H, 1,2,7,8-H, Ht), 7.06 (d, J=8.7 Hz, 8H, p-Ph), 6.82 (d, J=8.2 Hz, 8H, p-Ph), 6.63 (d, J=8.2 Hz, 8H, p-Ph), 6.49 (d, J=8.7 Hz, 8H, p-Ph), 5.86 (s, 4H, =CH), 4.27 (s, 2H, $NCH_2$), 3.84-3.81 (m, 12H, $OCH_3$), 3.77-3.74 (m, 12H, $OCH_3$), 1.87-1.83 (m, 2H, N $CH_2CH_2$), 1.44-1.39 (m, 2H, $NCH_2CH_2CH_2$), 0.96 (t, J=7.3 Hz, 3H, $CH_3$).

$^{13}$C NMR (100 MHz, $CDCl_3$ δ): 158.9, 158.6, 147.9, 143.7, 134.9, 133.2, 130.8, 128.9, 126.7, 117.6, 113.9, 113.1, 111.5, 109.0, 89.6, 84.5, 55.6 ($OCH_3$), 55.4 ($OCH_3$), 23.0 ($CH_2$), 20.7 ($CH_2$), 16.7 ($CH_2$), 14.1 ($CH_2$).

Elemental analysis: Calculated, %: C, 79.64; H, 6.27; N, 3.48. $C_{80}H_{75}N_3O_8$. Found, %: C, 79.44; H, 6.07; N, 3.28.

Example 8

9-(2-ethylhexyl)-3,6-bis{$N^3,N^3,N^6,N^6$-tetrakis(2,2-bis[4-methoxyphenyl)vinyl]amino}-9H-carbazole
(see Scheme 3, Compound 8 or V-1021)

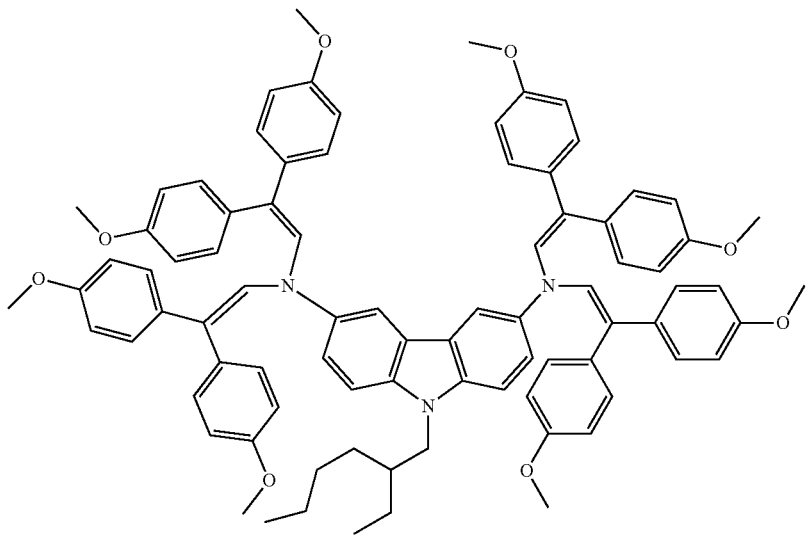

9-(2-ethylhexyl)carbazole-3,6-diamine (1 g, 3.2 mmol) is dissolved in toluene (17 ml), (+/−)10-camphorsulfonic acid (1 g, 4.3 mmol) was added and reaction mixture was refluxed for min. Then 2,2-bis(4-methoxyphenyl)acetaldehyde (4.1 g, 16 mmol) was added and reaction was continued using Dean-Stark apparatus for another 1.5 h. After reaction was finished (TLC, acetone:n-hexane/v:v, 1:4) reaction mixture was extracted with ethyl acetate, organic layer dried with anhydrous $Na_2SO_4$, filtered and organic solvents removed in vacuum. The residue was purified by column chromatography using acetone: n-hexane/v:v, 3:22 and precipitated from 20% solution in THF to 20-fold excess of methanol. Obtained material was dried under vacuum at 40° C. to yield 8 as yellow amorphous powder (2 g, 49%).

$^1$H NMR (400 MHz, $CDCl_3$ δ): 7.76 (s, 2H, 4,5-H, Ht), 7.35-7.26 (m, 4H, 1,2,7,8-H, Ht), 7.06 (d, J=8.6 Hz, 8H, p-Ph), 6.82 (d, J=8.3 Hz, 8H, p-Ph), 6.67-6.60 (m, 8H, p-Ph), 6.49 (d, J=8.6 Hz, 8H, p-Ph), 5.86 (s, 4H, =CH), 4.11 (d, J=8.3 Hz, 2H, $NCH_2$), 3.84 (s, 12H, $OCH_3$), 3.74 (s, 12H, $OCH_3$), 2.04 (s, 1H, $NCH_2CH$), 1.45-1.26 (m, 8H, $NCH_2CH(CH_2)4$), 0.91 (m, 6H, $(CH_3)2$).

$^{13}$C NMR (100 MHz, $CDCl_3$ δ): 158.9, 158.6, 144.2, 143.6, 140.6, 134.9, 133.2, 130.9, 129.6, 128.9, 128.0, 123.2, 119.7, 117.7, 117.6, 115.1, 114.6, 113.9, 113.1, 109.3, 89.5, 55.6 ($OCH_3$), 55.4 ($OCH_3$), 47.7 (CH), 39.6 ($CH_2$), 32.8 ($CH_2$), 31.1 ($CH_2$), 29.0 ($CH_2$), 23.3 ($CH_2$), 14.3 ($CH_3$), 11.0 ($CH_3$).

Elemental analysis: Calculated, %: C, 79.91; H, 6.63; N, 3.33. $C_{84}H_{83}N_3O_8$. Found, %: C, 79.71; H, 6.43; N, 3.13.

Example 9

$N^3,N^3,N^6,N^6$,9-pentakis(2,2-bis(4-methoxyphenyl)vinyl)-9H-carbazole-3,6-diamine (see Scheme 3, Compound 9 or V-1103)

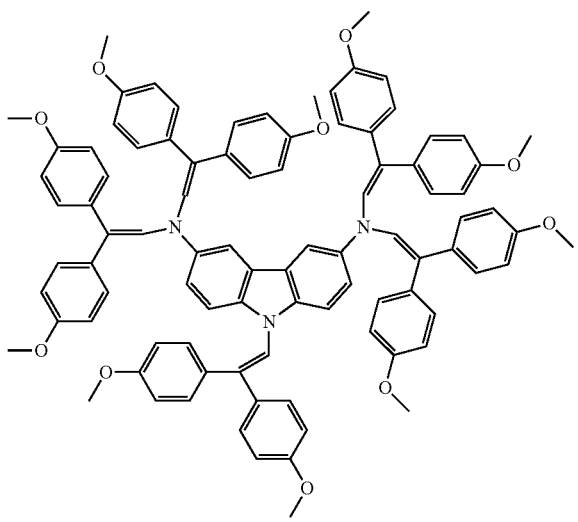

A mixture of 9H-carbazole-3,6-diamine (0.5 g, 2.5 mmol), 2,2-bis(4-methoxyphenyl)acetaldehyde (4.06 g, 15.8 mmol) and camphor-10-sulfonic acid (0.59 g, 2.5 mmol)

were dissolved in THF (10 ml+volume of the Dean-Stark trap ml), 3 Å molecular sieves were added to absorb water. The mixture was heated under argon for 8 hours at reflux. Afterwards (TLC control 7:18 v/v acetone/n-hexane) the reaction mixture was cooled to room temperature and poured into 200 ml of ethanol. The precipitate was filtered and washed with 200 ml of ethanol and then crystalized from acetone giving compound 9 as yellow crystals (m. p. 187-189° C.). Yield: 2.05 g (58%).

Elemental analysis calcd (%) for C92H81N3O10 (1387.59 g/mol): C, 79.57; H, 5.88; N, 3.03. Found: C, 79.31; H, 6.01; N, 3.16.

1H NMR (700 MHz, CDCl$_3$) δ 7.69 (s, 2H), 7.38 (d, 8.7 Hz, 2H), 7.18-7.10 (m, 4H), 7.04 (dd, J=28.6, 8.5 Hz, 10H), 6.97-6.88 (m, 2H), 6.86-6.75 (m, 8H), 6.70-6.55 (m, 11H), 6.53-6.42 (m, 8H), 5.81 (s, 4H), 3.89-3.69 (m, 30H).

13C NMR (176 MHz, CDCl3) δ 159.78, 158.87, 158.85, 158.50, 136.58, 134.61, 133.63, 133.00, 131.14, 130.80, 130.66, 130.15, 129.94, 129.68, 128.81, 127.68, 124.24, 117.27, 114.39, 113.80, 113.74, 112.97, 110.98, 108.74, 55.40, 55.40, 55.19.

Elemental analysis calcd (%) for C92H81N3O10 (1387.59 g/mol): C, 79.57; H, 5.88; N, 3.03. Found: C, 79.31; H, 6.01; N, 3.16.

Example 10

$N^2,N^2,N^7,N^7$-tetrakis[2,2-bis(4-methoxyphenyl)vinyl]-9H-fluorene-2,7-diamine (see Scheme 4, Compound 10 or V-1275)

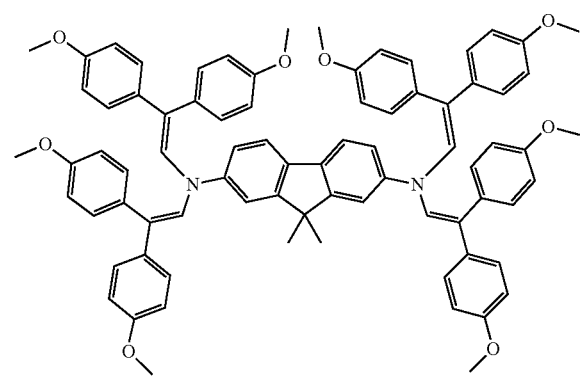

2,7-diaminofluorene (0.3 g, 1.5 mmol) was dissolved in tetrahydrofuran (9 ml+volume of the Dean-Stark trap), (+/−) camphor-10-sulphonic acid (0.36 g, 1.5 mmol) was added and the mixture was heated at reflux for 20 minutes. Afterwards, 2,2-bis(4-methoxyphenyl)acetaldehyde (2.4 g, 9.2 mmol) was added and reflux was continued using a Dean-Stark trap for 6 hours. After cooling to room temperature, reaction mixture was extracted with ethyl acetate. The organic layer was dried over anhydrous Na$_2$SO$_4$, filtered and solvent evaporated. The crude product was crystallized from ethanol (30 ml). The obtained crystals were filtered off and washed with hot ethanol for three times. The product was recrystallized from acetone/ethanol 1:1 gave as light yellow-green crystals (1.14 g, 60%). $^1$H NMR (400 MHz, CDCl$_3$) δ 7.60 (d, J=8.4 Hz, 2H), 7.34-7.20 (m, 2H), 7.19-6.94 (m, 10H), 6.84 (d, J=8.4 Hz, 8H), 6.67 (d, J=8.4 Hz, 8H), 6.49 (d, J=8.4 Hz, 8H), 5.82 (s, 4H), 4.04-3.57 (m, 26H).

$^{13}$C NMR (101 Mhz, CDCl$_3$) δ 159.01, 158.71, 144.37, 132.82, 130.66, 130.18, 128.85, 114.43, 113.92, 113.63, 113.05, 55.46, 55.26, 37.05 ppm.

Anal. calcd for C$_{77}$H$_{68}$N$_2$O$_8$: C, 80.46; H, 5.96; N, 2.44. found: C, 80.14; H, 5.82; N, 2.48.

Example 11

$N^2,N^2,N^7,N^7$-tetrakis[2,2-bis(4-methoxyphenyl)vinyl]-9,9-dimethyl-9H-fluorene-2,7-diamine (see Scheme 4, Compound 11 or V-1237)

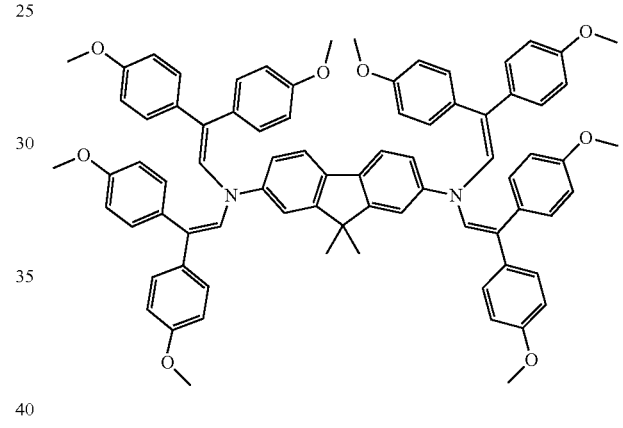

Compound 10 (0.5 g, 0.4 mmol) in dimethylsulfoxyde (20 ml) was dissolved and purged with argon for 30 minutes. Afterwards, benzyltriethylammonium chloride (0.01 g, 0.04 mmol) and 50% NaOH (0.15 ml) solution were added. The color of the reaction turned black and then iodomethane (0.14 g, 1.0 mmol) was slowly added dropwise under argon atmosphere and stirred at room temperature for 120 hours. The reaction mixture was filtered off and washed with water three times. The crude product was purified by column chromatography using 1:4 v/v tetrahydrofuran/n-hexane as an eluent to collect product 11 as a yellow solid (0.26 g, 51%).

$^1$H NMR (400 MHz, CDCl$_3$) δ 7.54 (d, J=8.0 Hz, 2H), 7.19-6.94 (m, 12H), 6.87 (d, J=8.4 Hz, 8H), 6.66 (d, J=8.4 Hz, 8H), 6.53 (d, J=8.4 Hz, 8H), 5.96-5.70 (m, 4H), 3.84 (d, J=36.8, 24H), 1.46 (s, 6H).

$^{13}$C NMR (101 MHz, CDCl$_3$) δ 158.98, 158.68, 155.02, 132.82, 132.23, 130.65, 128.90, 116.10, 113.90, 113.01, 111.03, 55.43, 55.24, 47.14, 27.56 ppm.

Anal. calcd for C$_{79}$H$_{72}$N$_2$O$_8$: C, 80.59; H, 6.16; N, 2.38. found: C, 80.74; H, 6.11; N, 2.35.

Example 12

N²,N²,N⁷,N⁷-tetrakis[2,2-bis(4-methoxyphenyl)vinyl]-9,9-dipropyl-9H-fluorene-2,7-diamine (see Scheme 4, Compound 12 or V-1235)

Example 13

N²,N²,N⁷,N⁷-tetrakis[2,2-bis(4-methoxyphenyl)vinyl]-9,9-dihexyl-9H-fluorene-2,7-diamine (see Scheme 4, Compound 13 or V-1236)

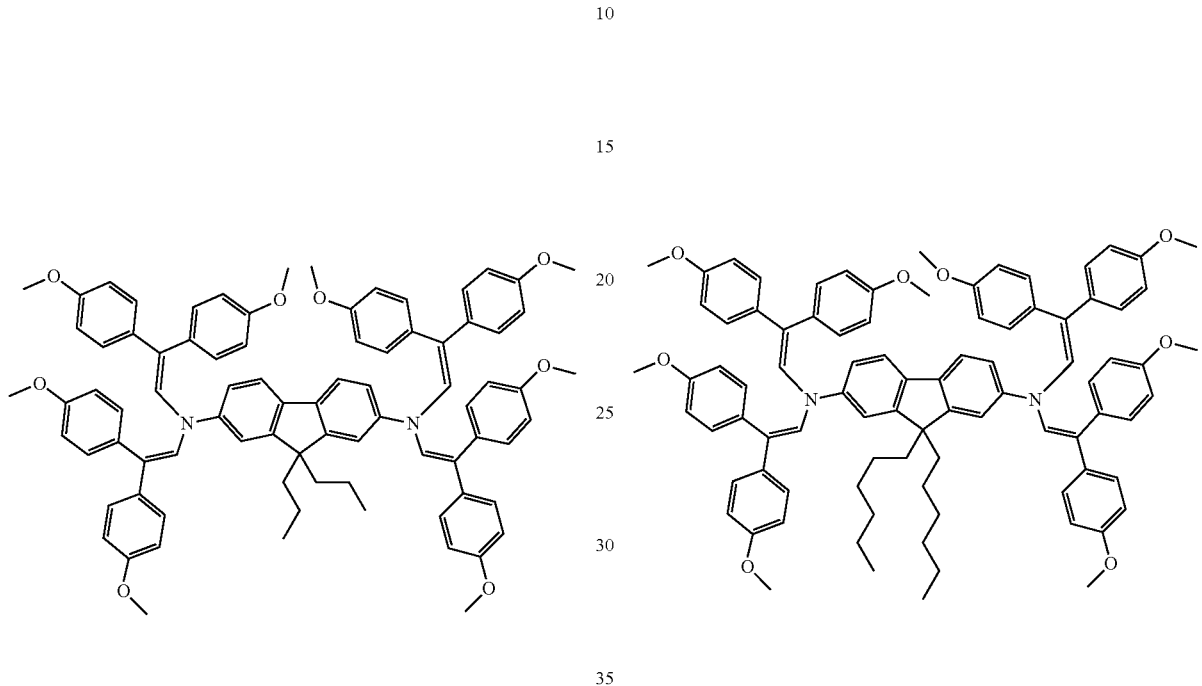

Compound 10 (0.5 g, 0.4 mmol) in dimethylsulfoxyde (20 ml) was dissolved and purged with argon for 30 minutes. Afterwards, benzyltriethylammonium chloride (0.01 g, 0.04 mmol) and 50% NaOH (0.15 ml) solution were added. The color of the reaction turned black and then bromopropane (0.12 g, 1.0 mmol) was slowly added dropwise under argon atmosphere and stirred at room temperature for 72 hours. The reaction mixture was filtered off and washed with water three times. The crude product was purified by column chromatography using 1:4 v/v tetrahydrofuran/n-hexane as an eluent to collect product 12 as a yellow solid (0.28 g, 52%).

¹H NMR (400 MHz, CDCl₃) δ 7.48 (d, J=8.0 Hz, 2H), 7.12-6.94 (m, 12H), 6.85 (d, J=8.8 Hz, 8H), 6.66 (d, J=8.8 Hz, 8H), 6.51 (d, J=8.8 Hz, 8H), 5.81 (s, 4H), 3.81 (d, J=37.2 Hz, 24H), 1.99-1.81 (m, 4H), 0.88-0.60 (m, 10H).

¹³C NMR (101 MHz, CDCl₃) δ 158.79, 158.54, 149.08, 134.23, 132.65, 130.45, 128.79, 119.03, 113.71, 112.84, 111.90, 59.52, 55.25, 55.07, 17.74, 14.12, 11.52 ppm.

Anal. calcd for $C_{83}H_{80}N_2O_8$: C, 80.82; H, 6.54; N, 2.27. found: C, 80.64; H, 6.61; N, 2.30.

Compound 10 (0.5 g, 0.4 mmol) in dimethylsulfoxyde (20 ml) was dissolved and purged with argon for 30 minutes. Afterwards, benzyltriethylammonium chloride (0.01 g, 0.04 mmol) and 50% NaOH (0.15 ml) solution were added. The color of the reaction turned black and then bromohexane (0.16 g, 1.0 mmol) was slowly added dropwise under argon atmosphere and stirred at room temperature for 26 hours. The reaction mixture was filtered off and washed repeatedly with water three times. The crude product was purified by column chromatography using 4:21 v/v tetrahydrofuran/n-hexane as an eluent to collect product 13 a yellow solid (0.36 g, 63%).

¹H NMR (400 MHz, CDCl₃) δ 7.52 (d, J=8.0 Hz, 2H), 7.12-6.93 (m, 12H), 6.85 (d, J=8.4 Hz, 8H), 6.65 (d, J=8.4 Hz, 8H), 6.50 (d, J=8.8 Hz, 8H), 5.81 (s, 4H), 3.81 (d, J=38.0 Hz, 24H), 1.97-1.82 (m, 4H), 1.21-1.01 (m, 12H), 0.85-0.66 (m, 10H) ppm.

¹³C NMR (101 MHz, CDCl₃) δ 158.99, 158.69, 152.04, 134.48, 132.95, 130.64, 128.90, 119.25, 115.91, 113.92, 113.02, 111.31, 55.38, 55.26, 40.11, 31.39, 29.38, 23.62, 22.48, 14.12 ppm.

Anal. calcd for $C_{89}H_{92}N_2O_8$: C, 81.12; H, 7.04; N, 2.13. found: C, 81.24; H, 7.11; N, 2.10.

Example 14

9,9-dibenzyl-$N^2,N^2,N^7,N^7$-tetrakis[2,2-bis(4-methoxyphenyl)vinyl]-9H-fluorene-2,7-diamine (see Scheme 4, Compound 14 or V-1227)

Example 15

N,N-bis[2,2-bis(4-methoxyphenyl)vinyl]-9,9'-spirobi[fluoren]-2-amine (see Scheme 5, Compound 15 or V-1305)

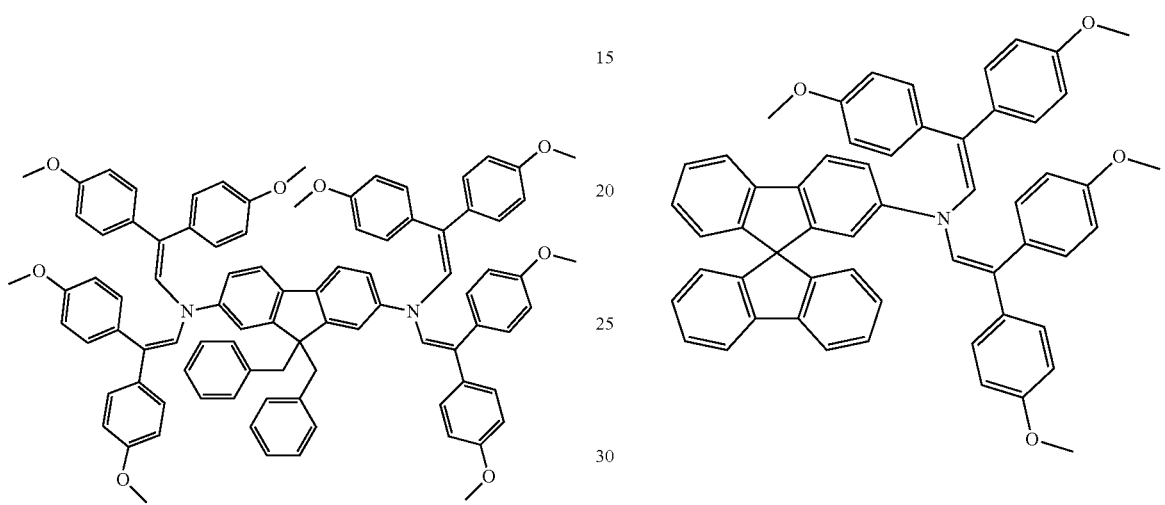

Compound 10 (0.5 g, 0.4 mmol) in dimethylsulfoxyde (20 ml) was dissolved and purged with argon for 30 minutes. Afterwards, benzyltriethylammonium chloride (0.01 g, 0.04 mmol) and 50% NaOH (0.15 ml) solution were added. The color of the reaction turned black and then benzyl bromide (0.16 g, 1.0 mmol) was slowly added dropwise under argon atmosphere and stirred at room temperature for 96 hours. The reaction mixture was filtered off and washed with water three times. The crude product was purified by column chromatography using 1:4 v/v tetrahydrofuran/n-hexane as an eluent to collect product 14 as a pale brown solid (0.29 g, 50%).

$^1$H NMR (400 MHz, acetone-$d_6$) δ 7.56 (d, J=8.0 Hz, 2H), 7.31-6.78 (m, 30H), 6.71 (d, J=8.4 Hz, 8H), 6.50 (d, J=8.4 Hz, 8H), 5.97-5.66 (m, 4H), 3.85 (d, J=48.8 Hz, 24H), 3.53-3.14 (m, 4H).

$^{13}$C NMR (101 MHz, acetone) δ 159.35, 159.03, 148.60, 136.29, 134.30, 132.53, 130.68, 130.54, 128.84, 127.22, 127.14, 126.52, 113.86, 113.50, 112.98, 60.05, 54.88, 54.61, 10.95 ppm.

Anal. calcd for $C_{91}H_{80}N_2O_8$: C, 82.20; H, 6.06; N, 2.11. found: C, 82.54; H, 6.11; N, 2.15.

9,9'-spirobi[9H-fluoren]-2-amine (0.30 g, 0.91 mmol) was dissolved in tetrahydrofuran (9 ml+volume of the Dean-Stark trap), (+/−)camphor-10-sulphonic acid (0.21 g, 0.91 mmol) was added and the mixture was heated at reflux for 20 minutes. Afterwards, 2,2-bis(4-methoxyphenyl)acetaldehyde (0.70 g, 2.72 mmol) was added, and reflux continued using a Dean-Stark trap. After termination of the reaction (6 h, TLC, THF:n-hexane, 7:18) the reaction mixture was extracted with ethyl acetate. The organic layer was dried over anhydrous $Na_2SO_4$, filtered and solvent evaporated. The crude product was purified by column chromatography using THF:n-hexane (v:v; 4:21) eluent. The obtained product was precipitated from THF into 20-fold excess of methanol. The precipitate was filtered off and washed with methanol to collect product 15 as a yellow solid (0.36 g, 49%).

$^1$H NMR (400 MHz, THF-$d_8$) δ: 7.83 (d, J=8.3 Hz, 1H); 7.79 (d, J=7.6 Hz, 3H); 7.33-7.21 (m, 3H); 7.16 (dd, J=8.3, 2.2 Hz, 1H); 7.09 (t, J=6.9 Hz, 2H); 6.94 (t, J=6.9 Hz, 1H); 6.85 (d, J=8.7 Hz, 4H); 6.77 (d, J=8.8 Hz, 4H); 6.72 (d, J=7.6 Hz, 2H); 6.53 (d, J=8.8 Hz, 4H); 6.50-6.46 (m, 2H); 6.33 (d, J=8.7 Hz, 4H); 5.60 (s, 2H); 3.78 (s, 6H); 3.66 (s, 6H) ppm.

$^{13}$C NMR (101 MHz, THF) δ: 160.44; 160.13; 151.16; 150.20; 150.12; 147.58; 142.88; 142.62; 137.27; 135.19; 133.62; 132.08; 131.50; 129.83; 128.66; 128.62; 128.49; 127.57; 127.49; 124.89; 124.41; 121.55; 121.01; 120.09; 118.07; 114.75; 113.76; 112.91; 66.50; 55.69; 55.44 ppm.

Anal. calcd for $C_{57}H_{45}NO_4$: C, 84.73; H, 5.61; N, 1.73. found: C, 84.59; H, 5.69; N, 1.92.

Example 16

N²,N²,N²',N²'-tetrakis[2,2-bis(4-methoxyphenyl)vinyl]-9,9'-spirobi[fluorene]-2,2'-diamine (see Scheme 5, Compound 16 or V-1306)

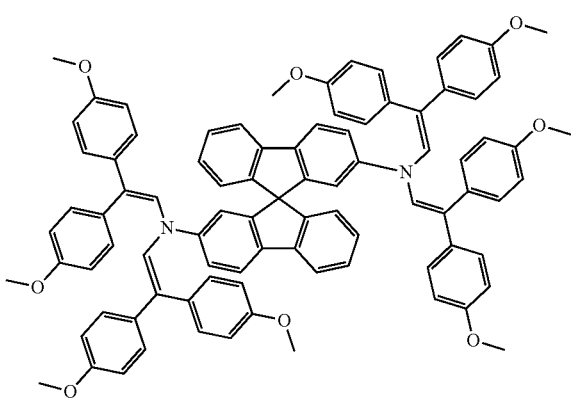

9,9'-spirobi[fluorene]-2,2'-diamine (0.20 g, 0.58 mmol) was dissolved in toluene (7 ml+volume of the Dean-Stark trap), (+/−)camphor-10-sulphonic acid (0.13 g, 0.58 mmol) was added and the mixture was heated at reflux for 20 minutes. Afterwards, 2,2-bis(4-methoxyphenyl)acetaldehyde (0.89 g, 3.46 mmol) was added, and reflux continued using a Dean-Stark trap. After termination of the reaction (6 h, TLC, THF:n-hexane, 2:3) the reaction mixture was extracted with dichloromethane. The organic layer was dried over anhydrous $Na_2SO_4$, filtered and solvent evaporated. The crude product was purified by column chromatography using THF:n-hexane (v:v; 7:18) eluent. The obtained product was precipitated from THF into 20-fold excess of methanol. The precipitate was filtered off and washed with methanol to collect product 16 as a yellow solid (0.23 g, 31%).

$^1$H NMR (400 MHz, THF-$d_8$) δ: 7.74 (d, J=8.3 Hz, 2H); 7.70 (d, J=7.6 Hz, 2H); 7.21 (t, J=7.0 Hz, 2H); 7.10 (dd, J=8.3, 2.2 Hz, 2H); 6.96 (t, J=7.5 Hz, 2H); 6.89 (d, J=8.8 Hz, 8H); 6.79 (d, J=8.8 Hz, 8H); 6.62-6.52 (m, 12H); 6.36 (d, J=8.8 Hz, 8H); 5.63 (s, 4H); 3.80 (s, 12H); 3.69 (s, 12H) ppm.

$^{13}$C NMR (101 MHz; THF) δ: 160.48; 160.17; 151.32; 150.51; 147.54; 142.40; 137.19; 135.13; 133.73; 132.28; 131.50; 129.88; 128.44; 127.69; 127.46; 124.33; 121.64; 120.08; 117.85; 114.90; 113.81; 112.52; 66.50; 55.72; 55.46 ppm.

Anal. calcd for $C_{89}H_{74}N_2O_8$: C, 82.26; H, 5.74; N, 2.16. found: C, 79.33; H, 6.66; N, 2.08.

Example 17

N²,N²,N⁷,N⁷-tetrakis[2,2-bis(4-methoxyphenyl)vinyl]-9,9'-spirobi[fluorene]-2,7-diamine (see Scheme 5, Compound 17 or V-1308)

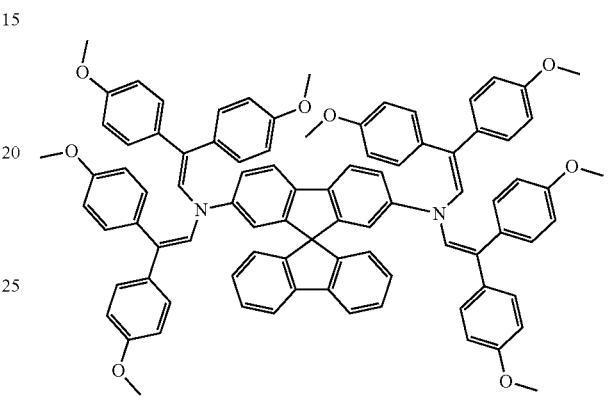

9,9'-spirobi[fluorene]-2,7-diamine (0.14 g, 0.42 mmol) was dissolved in toluene (5 ml+volume of the Dean-Stark trap), (+/−)camphor-10-sulphonic acid (0.10 g, 0.42 mmol) was added and the mixture was heated at reflux for 20 minutes. Afterwards, 2,2-bis(4-methoxyphenyl)acetaldehyde (0.64 g, 2.50 mmol) was added, and reflux continued using a Dean-Stark trap. After termination of the reaction (5 h, TLC, acetone:n-hexane, 7:18) the reaction mixture was extracted with ethyl acetate. The organic layer was dried over anhydrous $Na_2SO_4$, filtered and solvent evaporated. The crude product was purified by column chromatography using THF:n-hexane (v:v; 7:18) eluent. The obtained product was precipitated from THF into 20-fold excess of methanol. The precipitate was filtered off and washed with methanol to collect product 17 as a yellow solid (0.22 g, 42%).

$^1$H NMR (400 MHz, THF-$d_8$) δ: 7.75 (d, J=8.3 Hz, 2H); 7.68 (d, J=7.5 Hz, 2H); 7.23 (t, J=7.0 Hz, 2H); 7.11 (dd, J=8.2, 2.5 Hz, 4H); 6.87-6.72 (m, 18H); 6.52 (d, J=8.8 Hz, 8H); 6.32 (d, J=8.8 Hz, 10H); 5.56 (s, 4H); 3.78 (s, 12H); 3.66 (s, 12H) ppm.

$^{13}$C NMR (101 MHz, THF) δ: 160.39; 160.08; 151.35; 150.36; 146.67; 142.81; 137.14; 135.27; 133.68; 131.71; 131.52; 129.80; 128.62; 128.60; 127.65; 124.92; 121.12; 120.65; 118.22; 114.72; 113.74; 112.85; 66.50; 55.68; 55.42 ppm.

Anal. calcd for $C_{89}H_{74}N_2O_8$: C, 82.26; H, 5.74; N, 2.16. found: C, 82.14; H, 5.43; N, 2.5.

Example 18

N$^2$,N$^2$,N$^{2'}$,N$^{2'}$,N$^7$,N$^7$,N$^{7'}$,N$^{7'}$-octakis[2,2-bis(4-methoxyphenyl)vinyl]-9,9'-spirobi[fluorene]-2,2',7,7'-tetraamine (see Scheme 5, Compound 18 or V-1307)

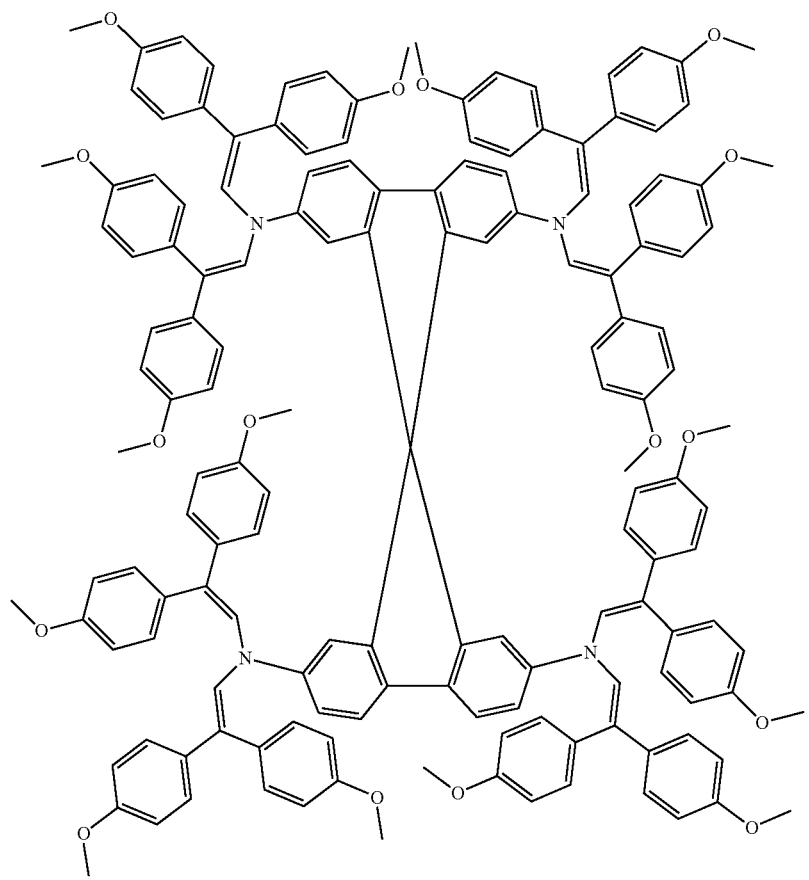

2,2',7,7'-Tetraamino-9,9'-spirobifluorene (0.20 g, 0.53 mmol) was dissolved in toluene (7 ml+volume of the Dean-Stark trap), (+/−)camphor-10-sulphonic acid (0.12 g, 0.53 mmol) was added and the mixture was heated at reflux for 20 minutes. Afterwards, 2,2-bis(4-methoxyphenyl)acetaldehyde (1.63 g, 6.36 mmol) was added, and reflux continued using a Dean-Stark trap. After termination of the reaction (5 h, TLC, acetone:n-hexane, 2:3) the reaction mixture was extracted with ethyl acetate. The organic layer was dried over anhydrous Na$_2$SO$_4$, filtered and solvent evaporated. The crude product was purified by column chromatography using acetone:n-hexane (v:v; 8:17) eluent. The obtained product was precipitated from THF into 20-fold excess of methanol. The precipitate was filtered off and washed with methanol to collect product 18 as a yellow solid (0.4 g, 33%).

$^1$H NMR (400 MHz, THF-d$_8$) δ: 7.55 (d, J=8.3 Hz, 4H); 6.98 (dd, J=8.3, 2.2 Hz, 4H); 6.91 (d, J=8.7 Hz, 16H); 6.83 (d, J=8.8 Hz, 16H); 6.61 (d, J=8.8 Hz, 16H); 6.50 (d, J=2.2 Hz, 4H); 6.40 (d, J=8.8 Hz, 16H); 5.65 (s, 8H); 3.86 (s, 24H); 3.70 (s, 24H) ppm.

$^{13}$C NMR (101 MHz, THF) δ: 160.49; 160.13; 151.90; 146.56; 136.85; 135.24; 133.90; 132.05; 131.53; 129.94; 127.92; 120.79; 117.79; 114.97; 113.82; 112.19; 66.50; 55.78; 55.45 ppm.

Anal. calcd for C$_{153}$H$_{132}$N$_4$O$_{16}$: C, 80.50; H, 5.83; N, 2.45. found: C, 77.9; H, 5.7; N, 2.46.

Example 19

Ionization Potential Measurements

The solid state ionization potential ($I_p$) of the layers of the compounds of formulae (1) to (18) was measured by the electron photoemission in air method (E. Miyamoto, Y. Yamaguchi, M. Masaaki, Electrophotography, 1989, vol. 28, pp. 364). The samples for the ionization potential measurement were prepared by dissolving materials in THF and were coated on Al plates pre-coated with ~0.5 µm thick methylmethacrylate and methacrylic acid copolymer adhesive layer. The thickness of the transporting material layer was $0.5^{-1}$ µm. Photoemission experiments are carried out in vacuum and high vacuum is one of the main requirements for these measurements. If vacuum is not high enough the sample surface oxidation and gas adsorption are influencing the measurement results. In our case, however, the organic materials investigated are stable enough to oxygen and the measurements may be carried out in the air. The samples were illuminated with monochromatic light from the quartz monochromator with deuterium lamp. The power of the incident light beam was $(2\text{-}5) \cdot 10^{-8}$ W. The negative voltage of −300 V was supplied to the sample substrate. The counter-electrode with the 4.5×15 mm² slit for illumination was placed at 8 mm distance from the sample surface. The counter-electrode was connected to the input of the BK2-16 type electrometer, working in the open input regime, for the photocurrent measurement. The $10^{-15}$-$10^{-12}$ A strong photocurrent was flowing in the circuit under illumination. The photocurrent I is strongly dependent on the incident light photon energy hν. The $I^{0.5}=f(h\nu)$ dependence was plotted. Usually the dependence of the photocurrent on incident light quanta energy is well described by linear relationship between $I^{0.5}$ and hν near the threshold. The linear part of this dependence was extrapolated to the hν axis and $I_p$ value was determined as the photon energy at the interception point. The $I_p$ results are presented in Table 1.

Example 20

Hole Drift Mobility Measurements

The samples for the hole mobility measurements were prepared by spin-coating the solutions of the synthesized compounds 1-18 on the polyester films with conductive Al layer. THF was used for 1-6, 9-18 compounds, as chlorobenzene for 7 and 8 compounds as well. The layer thickness was in the range of 5-10 µm. The hole drift mobility was measured by xerographic time of flight technique (XTOF) (Vaezi-Nejad, S. M., *Int. J. Electronics*, 1987, 62, No 3, 361-384). Electric field was created by positive corona charging. The charge carriers were generated at the layer surface by illumination with pulses of nitrogen laser (pulse duration was 2 ns, wavelength 337 nm). The layer surface potential decrease as a result of pulse illumination was up to 1-5% of initial potential before illumination. The capacitance probe that was connected to the wide frequency band electrometer measured the speed of the surface potential decrease dU/dt. The transit time $t_t$ was determined by the kink on the curve of the dU/dt transient in double logarithmic scale. The drift mobility was calculated by the formula $\mu=d^2/U_0 t_t$, where d is the layer thickness, $U_0$—the surface potential at the moment of illumination. The µ results are presented in Table 1.

TABLE 1

Ionization potential ($I_p$) and charge mobility values (µ) of the hole transporting compounds 1-18 and Spiro-OMeTAD

| No. | Formula | Ip, eV | Mobility $\mu_0$, cm²V⁻¹s⁻¹ (at 0 V/cm) | Mobility cm²V⁻¹s⁻¹ (at $6.4 \cdot 10^5$ V/cm) |
|---|---|---|---|---|
| 1 or V-950 | 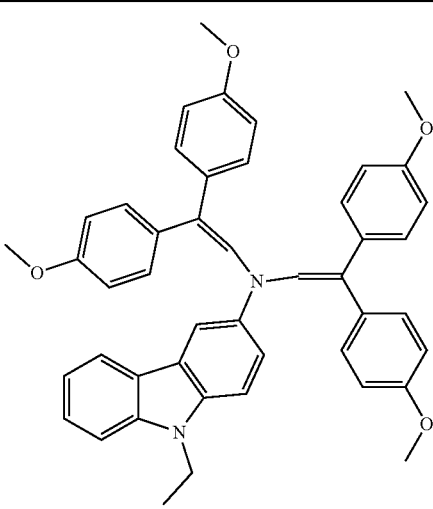 | 5.01 | $1.98 \cdot 10^{-5}$ | $8 \cdot 10^{-4}$ |

TABLE 1-continued

Ionization potential ($I_p$) and charge mobility values ($\mu$) of the hole transporting compounds 1-18 and Spiro-OMeTAD

| No. | Formula | $I_p$, eV | Mobility $\mu_0$, cm$^2$V$^{-1}$s$^{-1}$ (at 0 V/cm) | Mobility cm$^2$V$^{-1}$s$^{-1}$ (at $6.4 \cdot 10^5$ V/cm) |
|---|---|---|---|---|
| 2 or V-1013 | | 4.97 | $1.13 \cdot 10^{-5}$ | $5.5 \cdot 10^{-4}$ |
| 3 or V-1001 | | 5.01 | $2.7 \cdot 10^{-5}$ | $9.4 \cdot 10^{-4}$ |

TABLE 1-continued

Ionization potential ($I_p$) and charge mobility values ($\mu$) of the hole transporting compounds 1-18 and Spiro-OMeTAD

| No. | Formula | $I_p$, eV | Mobility $\mu_0$, cm$^2$V$^{-1}$s$^{-1}$ (at 0 V/cm) | Mobility cm$^2$V$^{-1}$s$^{-1}$ (at $6.4 \cdot 10^5$ V/cm) |
|---|---|---|---|---|
| 4 or V-1000 | | 5.00 | $3.2 \cdot 10^{-5}$ | $9 \cdot 10^{-4}$ |
| 5 or V-1004 | | 5.00 | $1.2 \cdot 10^{-5}$ | $4.6 \cdot 10^{-4}$ |

TABLE 1-continued
Ionization potential ($I_p$) and charge mobility values (μ) of the hole transporting compounds 1-18 and Spiro-OMeTAD
| No. | Formula | Ip, eV | Mobility $\mu_0$, $cm^2V^{-1}s^{-1}$ (at 0 V/cm) | Mobility $cm^2V^{-1}s^{-1}$ (at $6.4 \cdot 10^5$ V/cm) |
|---|---|---|---|---|
| 6 or V-1012 | 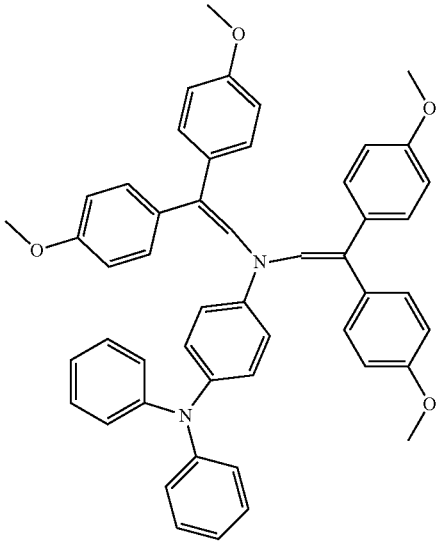 [SMILES: COc1ccc(C(=CN(C=C(c2ccc(OC)cc2)c2ccc(OC)cc2)c2ccc(N(c3ccccc3)c3ccccc3)cc2)c2ccc(OC)cc2)cc1] | 5.11 | $2.6 \cdot 10^{-5}$ | $5.0 \cdot 10^{-4}$ |
| 7 or V-1020 | 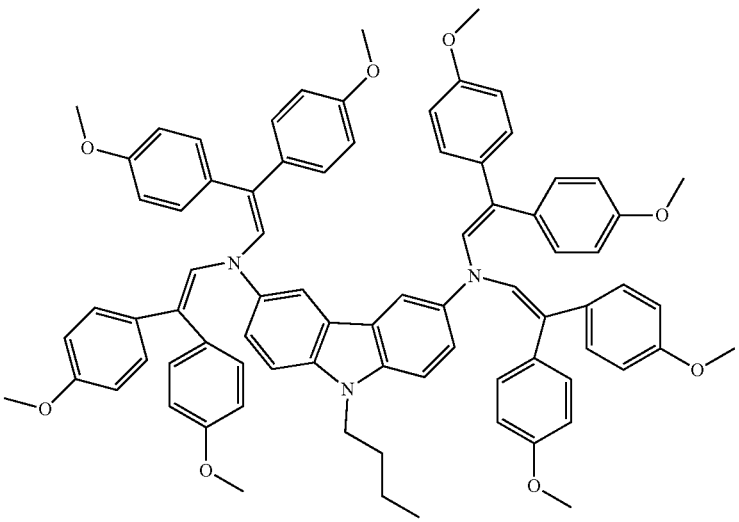 | 5.00 | $1.2 \cdot 10^{-4}$ | $1.1 \cdot 10^{-3}$ |

TABLE 1-continued
Ionization potential ($I_p$) and charge mobility values (µ) of the hole transporting compounds 1-18 and Spiro-OMeTAD
| No. | Formula | $I_p$, eV | Mobility $\mu_0$, cm$^2$V$^{-1}$s$^{-1}$ (at 0 V/cm) | Mobility cm$^2$V$^{-1}$s$^{-1}$ (at $6.4 \cdot 10^5$ V/cm) |
|---|---|---|---|---|
| 8 or V-2021 | 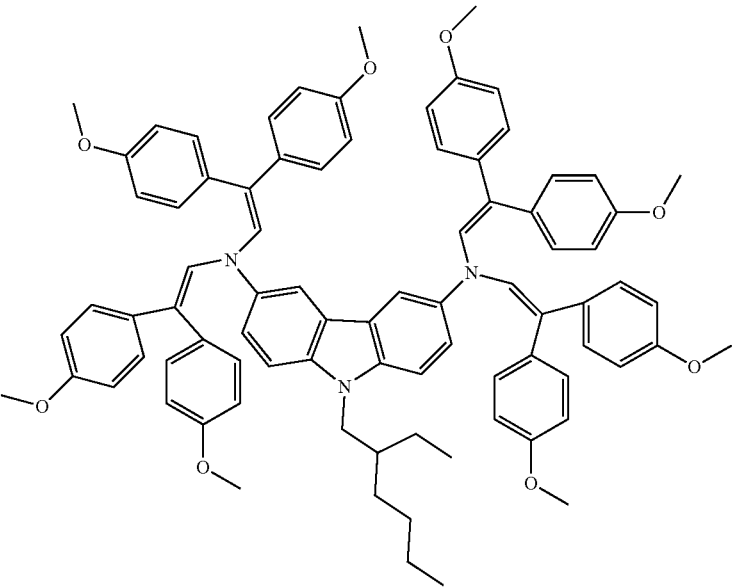 | 4.93 | $6 \cdot 10^{-5}$ | $2.1 \cdot 10^{-3}$ |
| 9 or V-1103 | 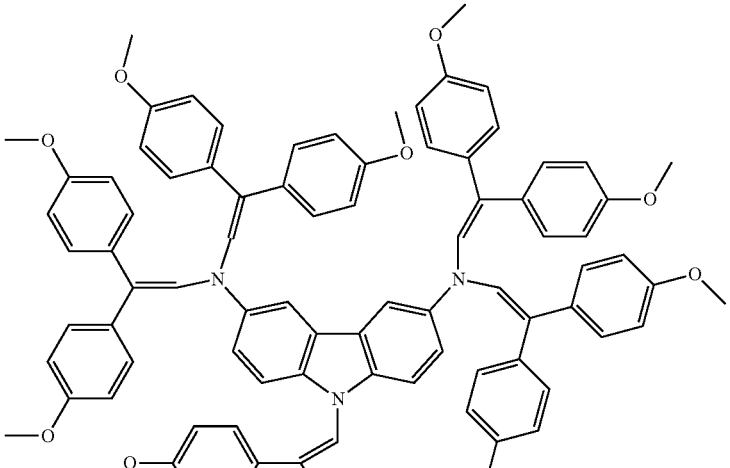 | 5.01 | $3.7 \cdot 10^{-5}$ | $7.8 \cdot 10^{-4}$ |

TABLE 1-continued
Ionization potential ($I_p$) and charge mobility values ($\mu$) of the hole transporting compounds 1-18 and Spiro-OMeTAD
| No. | Formula | Ip, eV | Mobility $\mu_0$, cm$^2$V$^{-1}$s$^{-1}$ (at 0 V/cm) | Mobility cm$^2$V$^{-1}$s$^{-1}$ (at 6.4 · 10$^5$ V/cm) |
|---|---|---|---|---|
| 10 or V-1275 | 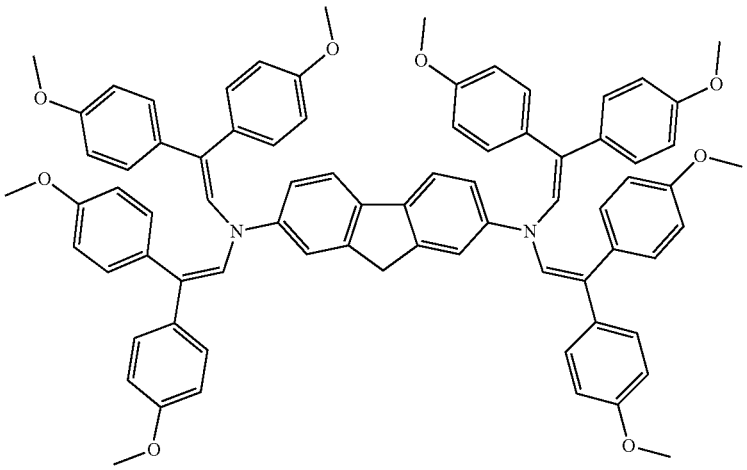 | 5.01 | 1.2 · 10$^{-4}$ | 5.3 · 10$^{-3}$ |
| 11 or V-1237 | 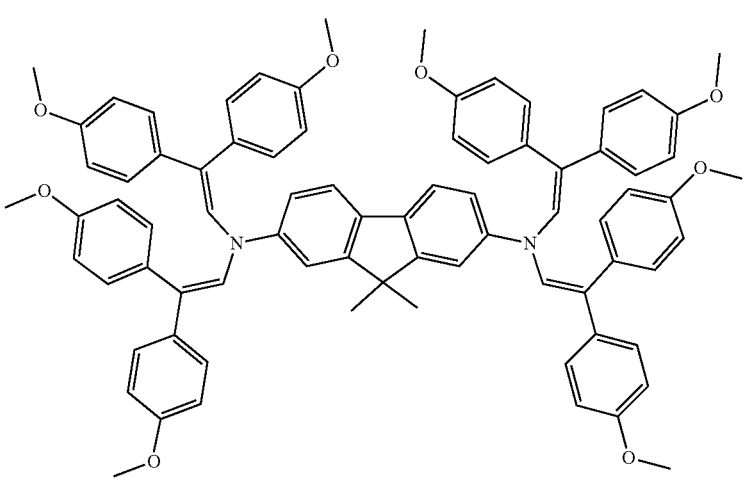 | 5.0 | 1.2 · 10$^{-4}$ | 3.8 · 10$^{-3}$ |
| 12 or V-1235 | 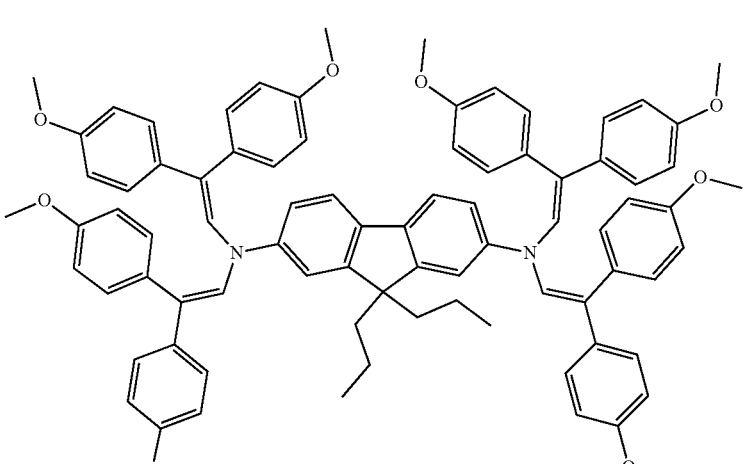 | 5.03 | 3.3 · 10$^{-4}$ | 2.8 · 10$^{-3}$ |

TABLE 1-continued

Ionization potential ($I_p$) and charge mobility values (μ) of the hole transporting compounds 1-18 and Spiro-OMeTAD

| No. | Formula | $I_p$, eV | Mobility $\mu_0$, cm$^2$V$^{-1}$s$^{-1}$ (at 0 V/cm) | Mobility cm$^2$V$^{-1}$s$^{-1}$ (at 6.4 · 10$^5$ V/cm) |
|---|---|---|---|---|
| 13 or V-1236 | | 5.03 | 2.6 · 10$^{-4}$ | 3.6 · 10$^{-3}$ |
| 14 or V-1227 | | 4.9 | 8.0 · 10$^{-5}$ | 1.6 · 10$^{-3}$ |
| 15 or V-1305 | | 5.2 | 1.7 · 10$^{-5}$ | 2.6 · 10$^{-4}$ |

TABLE 1-continued

Ionization potential ($I_p$) and charge mobility values ($\mu$) of the hole transporting compounds 1-18 and Spiro-OMeTAD

| No. | Formula | Ip, eV | Mobility $\mu_0$, cm$^2$V$^{-1}$s$^{-1}$ (at 0 V/cm) | Mobility cm$^2$V$^{-1}$s$^{-1}$ (at 6.4 · 10$^5$ V/cm) |
|---|---|---|---|---|
| 16 or V-1306 | | 5.2 | 5.4 · 10$^{-6}$ | 2.3 · 10$^{-4}$ |
| 17 or V-1308 | | 5.0 | 9.4 · 10$^{-4}$ | 2.1 · 10$^{-3}$ |

TABLE 1-continued

Ionization potential (I$_p$) and charge mobility values (µ) of the hole transporting compounds 1-18 and Spiro-OMeTAD

| No. | Formula | Ip, eV | Mobility µ$_0$, cm$^2$V$^{-1}$s$^{-1}$ (at 0 V/cm) | Mobility cm$^2$V$^{-1}$s$^{-1}$ (at 6.4 · 10$^5$ V/cm) |
|---|---|---|---|---|
| 18 or V-1307 | V1307 | 5.0 | 6.4 · 10$^{-4}$ | 1.4 · 10$^{-3}$ |
| Spiro-OMeTAD | | 5.00 | 4.1 · 10$^{-5}$ | 5 · 10$^{-4}$ |

The estimated $I_p$ values of all synthesized compounds are in range 4.90 eV-5.20 eV and are very closed to the value of Spiro-OMeTAD (5.0 eV). The measured charge mobility values of synthesized compounds 1-6, 8, 9, and 14-16 are also comparable to the values measured for Spiro-OMeTAD, while charge mobility of the compounds 7, 10-13, 17, and 18 increase by c.a. one order of magnitude ($\mu_0=10^{-4}$ cm$^2$ V$^{-1}$ S$^{-1}$) at weak electric fields.

Example 21

Photovoltaic Characterization of Compound of Formula (I) Corresponding to Compound V-950

Figure 2:
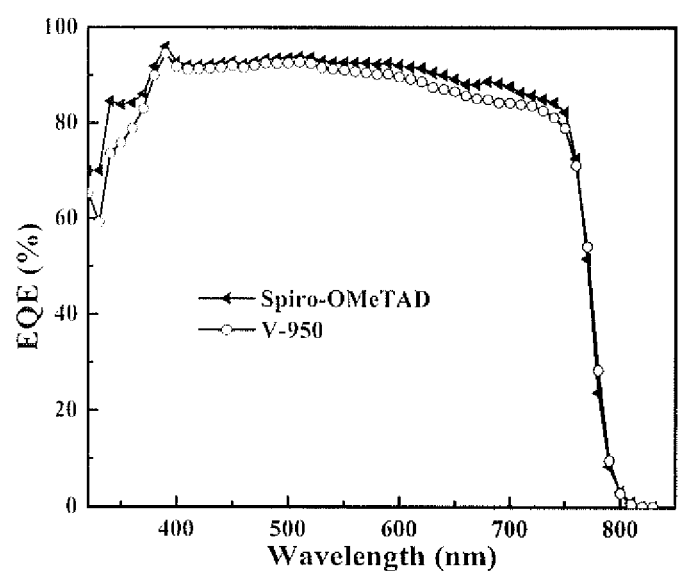
FIG. 2 shows the incident photon to current efficiency (IPCE) curve of solar cells where compound (1) corresponding to compound V-950 and Spiro-OMeTAD are explored as hole transporting materials.

The performance of hole transporter V-950 is tested in mixed perovskite-based solar cells using a mesoporous TiO$_2$ photo-anode and an Au cathode (FTO/compact TiO$_2$/mesoporous compact TiO$_2$/mixed perovskite/V-950/Au), following a procedure described in the literature (T. J. Jacobsson, J. P. Correa-Baena, M. Pazoki, M. Saliba, K. Schenk, M. Gratzel and A. Hagfeldt. Energy Environ. Sci., 2016, 9, 1706-1724). The mixtures of cations (methyl ammonia (MA), formamidinium (FA)) and anions (I, Br) were used for preparation of the mixed perovskite. The obtained device shows a maximum PCE of 17.8% under AM 1.5 G illumination. The measured fill factor is 0.74, the current density ($J_{SC}$) 22.5 mA/cm$^2$ and the open-circuit voltage ($V_{OC}$) is found to be 1.07 V (FIG. 1). The high $J_{SC}$ indicates that the photogenerated charge carriers are efficiently extracted and the high $V_{OC}$ reveals possibly good energy level alignment between perovskite valence band and the HOMO of V-950. This high $V_{OC}$ also indicates slow recombination between injected holes and electrons from either the perovskite capping layer or TiO$_2$. Current Density-Voltage (J-V) characteristics of compound (1) corresponding to compound V-950 and Spiro-OMeTAD are presented in FIG. 1. The incident photon-to-current efficiency (IPCE) (FIG. 2) of the device as a function of wavelength indicates that the device with V950 as the HTM exhibits IPCE above 90% from 400 nm covering the entire visible region to 700 nm.

The device characteristics demonstrate that performance of the investigated HTM is on par with Spiro-OMeTAD.

The invention claimed is:
1. A compound of formula (I):

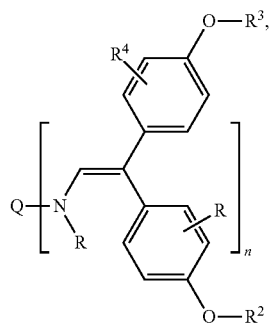

wherein
n is 1, 2, 3, 4, 5, 6, 7 or 8;
Q is a mono- or polycyclic system comprising at least one pair of a conjugated double bond (—C=C—C=C—), the polycyclic system comprising fused aromatic rings or monocyclic aromatic rings bound together by covalent bond or heteroaromatic system with N, O, S, Se, Si heteroatoms; wherein
said mono- or polycyclic system being substituted by H, halogen, cyano group, C1-C20 cyanoalkyl group, C1-C20 alkyl, C1-C20 alkoxy group, C1-C20 alkoxyalkyl, C1-C20 haloalkyl group, C1-C20 haloalkoxyalkyl, wherein said cyanoalkyl, alkyl, alkoxy, alkoxyalkyl, haloalkyl, haloalkoxyalkyl, C4-C20 aryl, C4-C20 alkylaryl, C4-C20 alkoxyaryl, C4-C20 alkenylarylalkyl, C4-C20 alkoxyarylalkenyl, C4-C20 bisalkoxyarylalkenylo groups if the groups comprise 3 or more carbons, the groups are linear, branched or cyclic, wherein halogen is selected from Cl, F, Br, or I;
R is a substituent, on each occurrence, identically or differently selected from C1-C20 alkyl, C2-C20 alkenyl, C4-C20 arylalkenyl, C4-C20 aryl groups, wherein said aryl and arylalkenyl groups are unsubstituted or substituted with C1-C20 alkyl or C1-C20 alkoxy groups, if the groups comprise 3 or more carbons, the groups are linear, branched or cyclic;
R$^1$, R$^2$, R$^3$, R$^4$ are independent one from another and selected from hydrogen, halogen, cyano, C1-C20 cyanoalkyl, C1-C20 alkyl, C1-C20 alkoxy, C1-C20 alkoxyalkyl, C1-C20 haloalkyl, C1-C20 haloalkoxyalkyl groups, if the groups comprise 3 or more carbons, the groups are linear, branched or cyclic, wherein halogen is selected from Cl, F, Br, or wherein the compound of formula (I) is selected from any one of compounds:
9-ethyl-3-{N,N-bis[2,2-bis(4-methoxyphenyl)vinyl] amino}-9H-carbazole (1);
9-butyl-3-{N,N-bis[2,2-bis(4-methoxyphenyl)vinyl] amino}-9H-carbazole (2);
9-hexyl-3-{N,N-bis[2,2-bis(4-methoxyphenyl)vinyl] amino}-9H-carbazole (3);
9-(2-ethylhexyl)-3-{N,N-bis[2,2-bis(4-methoxyphenyl)vinyl]amino}-9H-carbazole (4);
9-butyl-6-(-butyl)-3-{N,N-[2,2-bis(4-methoxyphenyl) vinyl]amino}-9H-carbazole (5);
4-{N,N-bis[2,2-bis(4-methoxyphenyl)vinyl] amino}triphenylamine (6);
9-butyl-3,6-bis{N$^3$,N$^3$,N$^6$,N$^6$-tetrakis(2,2-bis[4-methoxyphenyl)vinyl]amino}-9H-carbazole (7);
9-(2-ethylhexyl)-3,6-bis{N$^3$,N$^3$,N$^6$,N$^6$-tetrakis(2,2-bis [4-methoxyphenyl)vinyl]-amino}-9H-carbazole (8);
N$^3$,N$^3$,N$^6$,N$^6$,9-pentakis(2,2-bis(4-methoxyphenyl)vinyl)-9H-carbazole-3,6-diamine (9);
N$^2$,N$^2$,N$^7$,N$^7$-tetrakis[2,2-bis(4-methoxyphenyl)vinyl]-9H-fluorene-2,7-diamine (10);
N$^2$,N$^2$,N$^7$,N$^7$-tetrakis[2,2-bis(4-methoxyphenyl)vinyl]-9,9-dimethyl-9H-fluorene-2,7-diamine (11);
N$^2$,N$^2$,N$^7$,N$^7$-tetrakis[2,2-bis(4-methoxyphenyl)vinyl]-9,9-dipropyl-9H-fluorene-2,7-diamine (12);
N$^2$,N$^2$,N$^7$,N$^7$-tetrakis[2,2-bis(4-methoxyphenyl)vinyl]-9,9-dihexyl-9H-fluorene-2,7-diamine (13);
9,9-dibenzyl-N$^2$,N$^2$,N$^7$,N$^7$-tetrakis[2,2-bis(4-methoxyphenyl)vinyl]-9H-fluorene-2,7-diamine (14);
N,N-bis[2,2-bis(4-methoxyphenyl)vinyl]-9,9'-spirobi [fluoren]-2-amine (15);
N$^2$,N$^2$,N$^{2'}$,N$^{2'}$-tetrakis[2,2-bis(4-methoxyphenyl)vinyl]-9,9'-spirobi[fluorene]-2,2'-diamine (16);
N$^2$,N$^2$,N$^7$,N$^7$-tetrakis[2,2-bis(4-methoxyphenyl)vinyl]-9,9'-spirobi[fluorene]-2,7-diamine (17);
N$^2$,N$^2$,N$^{2'}$,N$^{2'}$,N$^7$,N$^7$,N$^{7'}$,N$^{7'}$-octakis[2,2-bis(4-methoxyphenyl)vinyl]-9,9'-spirobi[fluorene]-2,2',7, 7'-tetraamine (18).

2. The compound of formula (I) according to claim 1 for use in a photovoltaic device as nonpolymeric hole transporting materials.

3. The hole transporting material comprising at least one small molecule hole transporting material being selected from one of compounds of formula (I) according to claim 2.

4. The photovoltaic device comprising a compound of formula (I) according to claim 2.

5. A hole transporting material comprising at least one small molecule hole transporting material being selected from one of compounds of formula (I) according to claim 1.

6. A method of using a compound according to claim 1 as a hole transporting material in photovoltaic device.

7. The compound of the formula (I) according to claim 1 for use in photovoltaic device as nonpolymeric hole transporting materials.

8. The hole transporting material comprising at least one small molecule hole transporting material being selected from one of compounds of formula (I) according to claim 7.

9. The photovoltaic device comprising a compound of formula (I) according to claim 7.

10. The hole transporting material comprising at least one small molecule hole transporting material being selected from one of compounds of formula (I) according to claim 1.

11. The photovoltaic device comprising a compound of formula (I) according to claim 1.

12. A photovoltaic device comprising a compound of formula (I), wherein the compound is selected from any one of compounds:
   9-ethyl-3-{N,N-bis[2,2-bis(4-methoxyphenyl)vinyl]amino}-9H-carbazole (1);
   9-butyl-3-{N,N-bis[2,2-bis(4-methoxyphenyl)vinyl]amino}-9H-carbazole (2);
   9-hexyl-3-{N,N-bis[2,2-bis(4-methoxyphenyl)vinyl]amino}-9H-carbazole (3);
   9-(2-ethylhexyl)-3-{N,N-bis[2,2-bis(4-methoxyphenyl)vinyl]amino}-9H-carbazole (4);
   9-butyl-6-(-butyl)-3-{N,N-[2,2-bis(4-methoxyphenyl)vinyl]amino}-9H-carbazole (5);
   4-{N,N-bis[2,2-bis(4-methoxyphenyl)vinyl]amino}triphenylamine (6);
   9-butyl-3,6-bis{$N^3,N^3,N^6,N^6$-tetrakis(2,2bis[4-methoxyphenyl)vinyl]amino}-9H-carbazole (7);
   9-(2-ethylhexyl)-3,6-bis{$N^3,N^3,N^6,N^6$-tetrakis(2,2-bis[4-methoxyphenyl)vinyl]-amino}-9H-carbazole (8);
   $N^3,N^3,N^6,N^6$,9-pentakis(2,2-bis(4-methoxyphenyl)vinyl)-9H-carbazole-3,6-diamine (9);
   $N^2,N^2,N^7,N^7$-tetrakis[2,2-bis(4-methoxyphenyl)vinyl]-9H-fluorene-2,7-diamine (10);
   $N^2,N^2,N^7,N^7$-tetrakis[2,2-bis(4-methoxyphenyl)vinyl]-9,9-dimethyl-9H-fluorene-2,7-diamine (11);
   $N^2,N^2,N^7,N^7$-tetrakis[2,2-bis(4-methoxyphenyl)vinyl]-9,9-dipropyl-9H-fluorene-2,7-diamine (12);
   $N^2,N^2,N^7,N^7$-tetrakis[2,2-bis(4-methoxyphenyl)vinyl]-9,9-dihexyl-9H-fluorene-2,7-diamine (13);
   9,9-dibenzyl-$N^2,N^2,N^7,N^7$-tetrakis[2,2-bis(4-methoxyphenyl)vinyl]-9H-fluorene-2,7-diamine (14);
   N,N-bis[2,2-bis(4-methoxyphenyl)vinyl]-9,9'-spirobi[fluoren]-2-amine (15);
   $N^2,N^2,N^{2'},N^{2'}$-tetrakis[2,2-bis(4-methoxyphenyl)vinyl]-9,9'-spirobi[fluorene]-2,2'-diamine (16);
   $N^2,N^2,N^7,N^7$-tetrakis[2,2-bis(4-methoxyphenyl)vinyl]-9,9'-spirobi[fluorene]-2,7-diamine (17);
   $N^2,N^2,N^{2'},N^{2'},N^7,N^7,N^{7'},N^{7'}$-octakis[2,2-bis(4-methoxyphenyl)vinyl]-9,9'-spirobi[fluorene]-2,2',7,7'-tetraamine (18).

13. The photovoltaic device according to claim 12, comprising a hole transporting material, wherein said hole transporting material comprises the compound of formula (I).

14. The photovoltaic device according to claim 13 which is a solid state solar cell comprising an organic-inorganic perovskite as sensitizer under the form of a layer.

15. The photovoltaic device according to claim 14, wherein the organic-inorganic perovskite layer material comprises a perovskite-structure of formula (II):

$$AMX_3 \qquad (II)$$

wherein
A is an alkali metal ion, wherein one or more hydrogens are substituted by alkyl or acyl group, wherein said-ammonium ions, include mono, di, tri and tetra alkyl ammonium ions, wherein one or more hydrogens are substituted by alkyl group, wherein said ammonium ions, include amidinium, N-alkyl amidinium and imidinium ions, wherein one or more hydrogens are substituted by alkyl group, wherein the hydrogen atoms in the organic cations A are substituted by halogens selected from the group consisting of F, Cl, I and Br,
M is a divalent metal cation selected from the group consisting of $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, $EU^{2+}$, or $Yb^{2+}$; and
X is monovalent anion, independently selected from the group consisting of $Cl^-$, $Br^-$, I, $NCS^-$, $CN^-$, and $NCO^-$.

16. The photovoltaic device according to claim 15, wherein the organic-inorganic perovskite layer material comprises a perovskite-structure of formula (II):

$$AMX_3 \qquad (II)$$

wherein
A is an alkali metal ion, is $Li^+$, $Na^+$, $K^+$, $Rb^+$, $Cs^+$; ammonium or formamidium ion, wherein one or more hydrogens are substituted by alkyl or acyl group, wherein-said ammonium ions, include mono, di, tri and tetra alkyl ammonium ions, wherein one or more hydrogens are substituted by alkyl group, the substituent is alkyl group or groups independently selected from C1-C6, is methyl or ethyl groups, wherein said ammonium ions, include amidinium, N-alkyl amidinium and imidinium ions, wherein one or more hydrogens are substituted by alkyl group, the amidinium or imidinium ions are selected from C1-C6 carboxamide groups, formamidium or acetamidium groups, wherein the hydrogen atoms in the organic cations A may be substituted by halogens selected from the group consisting of F, Cl, I and Br, are-F or Cl; A is $Cs^+$ or methyl ammonium ion ($MA^+$), or formamidium ion ($FA^+$);
M is a divalent metal cation selected from the group consisting of $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, $EU^{2+}$, or $Yb^{2+}$; are $Pb^{2+}$, $Sn^{2+}$; and
X is monovalent anion, independently selected from the group consisting of $Cl^-$, $Br^-$, I, $NCS^-$, $CN^-$, and $NCO^-$; are $Cl^-$, $Br^-$, $I^-$.

17. The photovoltaic device according to claim 14, wherein the organic-inorganic perovskite layer material comprises a mixed perovskite-structure of the formulae (III) below:

$$A^1{}_{1-y}A^2{}_y PbX^1{}_{3-z}X^2{}_z \qquad (III)$$

wherein:

A¹ and A² are organic monovalent cations as defined for A, wherein

A is an alkali metal ion, wherein one or more hydrogens are substituted by alkyl or acyl group, wherein said ammonium ions, include mono, di, tri and tetra alkyl ammonium ions, wherein one or more hydrogens are substituted by alkyl group, wherein said ammonium ions, include amidinium, N-alkyl amidinium and imidinium ions, wherein one or more hydrogens are substituted by alkyl group, wherein the hydrogen atoms in the organic cations A are substituted by halogens selected from the group consisting of F, Cl, I and Br;

$X^1$ and $X^2$ are the same or different monovalent anions selected from the group consisting of Cl⁻, Br⁻, I⁻, NCS⁻, CN⁻ and NCO⁻;

y is in the interval between 0.1 and 0.9; and z is in the interval between 0.2 and 2.

18. The photovoltaic device according to claim 17, wherein the organic-inorganic perovskite layer material comprises a mixed perovskite-structure of the formulae (III) below:

$$A^1_{1-y}A^2_yPbX^1_{3-z}X^2_z \quad (III)$$

wherein:

A¹ and A² are organic monovalent cations as defined for A, wherein:

A is an alkali metal ion, is Li⁺, Na⁺, K⁺, Rb⁺, Cs⁺; ammonium or formamidium ion, wherein one or more hydrogens are substituted by alkyl or acyl group, wherein-said ammonium ions, include mono, di, tri and tetra alkyl ammonium ions, wherein one or more hydrogens are substituted by alkyl group, the substituent is alkyl group or groups independently selected from C1-C6, is methyl or ethyl groups, wherein said ammonium ions, include amidinium, N-alkyl amidinium and imidinium ions, wherein one or more hydrogens are substituted by alkyl group, the amidinium or imidinium ions are selected from C1-C6 carboxamide groups, are formamidium or acetamidium groups, wherein the hydrogen atoms in the organic cations A are substituted by halogens selected from the group consisting of F, Cl, I and Br, are-F or Cl; A is Cs⁺ or methyl ammonium ion (MA⁺), or formamidium ion (FA⁺);

M is a divalent metal cation selected from the group consisting of Cu²⁺, Ni²⁺, Co²⁺, Fe²⁺, Mn²⁺, Cr²⁺, Pd²⁺, Cd²⁺, Ge²⁺, Sn²⁺, Pb²⁺, EU²⁺, or Yb²⁺; are Pb²⁺, Sn²⁺; and X is monovalent anion, independently selected from the group consisting of Cl⁻, Br⁻, I, NCS⁻, CN⁻, and NCO⁻; are Cl⁻, Br⁻, I⁻:

$X^1$ and $X^2$ are the same or different monovalent anions selected from the group consisting of Cl⁻, Br⁻, I⁻, NCS⁻, CN⁻ and NCO⁻;

y is in the interval between 0.1 and 0.9; and z is in the interval between 0.2 and 2.

19. The photovoltaic device according to claim 13, which is a solid state solar cell comprising an organic-inorganic perovskite as sensitizer under the form of a layer and coated by the compound of formula (I)

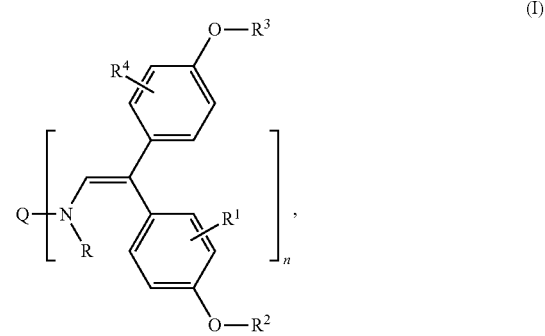

under the form of a layer.

20. The photovoltaic device according to claim 13 which is selected from an organic photovoltaic device, a photovoltaic solid state device, an p-n heterojunction, an organic solar cell, a dye sensitized solar cell, and solid state solar cell.

21. The photovoltaic device according to claim 12 which is selected from an organic photovoltaic device, a photovoltaic solid state device, an pn heterojunction, an organic solar cell, a dye sensitized solar cell, and solid state solar cell.

* * * * *